US007129055B2

(12) United States Patent
Littman et al.

(10) Patent No.: US 7,129,055 B2
(45) Date of Patent: *Oct. 31, 2006

(54) METHODS OF IDENTIFYING G-COUPLE RECEPTORS ASSOCIATED WITH MACROPHAGE-TROPHIC HIV, AND DIAGNOSTIC AND THERAPEUTIC USES THEREOF

(75) Inventors: Dan R. Littman, New York, NY (US); Hongkui Deng, Worcester, MA (US); Wilfried Ellmeier, New York, NY (US); Nathaniel R. Landau, New York, NY (US); Rong Liu, New York, NY (US)

(73) Assignee: New York University, New York, NY (US)

( * ) Notice: Subject to any disclaimer, the term of this patent is extended or adjusted under 35 U.S.C. 154(b) by 732 days.

This patent is subject to a terminal disclaimer.

(21) Appl. No.: 09/734,221

(22) Filed: Dec. 11, 2000

(65) Prior Publication Data
US 2003/0096221 A1    May 22, 2003

Related U.S. Application Data

(63) Continuation of application No. 08/861,105, filed on May 21, 1997, now Pat. No. 6,258,527, which is a continuation-in-part of application No. 08/858,660, filed on May 19, 1997, now abandoned.

(60) Provisional application No. 60/017,157, filed on May 20, 1996, provisional application No. 60/020,043, filed on Jun. 19, 1996.

(51) Int. Cl.
*C01N 33/53* (2006.01)
*C01N 33/533* (2006.01)
*C12N 15/00* (2006.01)
*C12N 15/48* (2006.01)
*C12N 15/07* (2006.01)
*C12N 15/09* (2006.01)
*C12N 5/28* (2006.01)
*C07K 16/28* (2006.01)

(52) U.S. Cl. ..................... 435/7.2; 435/7.21; 435/7.24; 435/7.8; 435/7.93; 435/325; 435/69.1; 435/440; 530/388.22

(58) Field of Classification Search .................. 435/5, 435/6, 7.1, 7.2, 7.21, 325, 366, 372, 372.2, 435/69.1, 7.93, 7.8, 8, 70.2, 7, 1, 7.3, 320, 435/440, 7.24; 424/85.1, 208.1; 530/388.22
See application file for complete search history.

(56) References Cited

U.S. PATENT DOCUMENTS 5,695,993 A    12/1997    Fukudome et al.

FOREIGN PATENT DOCUMENTS

| WO | WO 94/24282 | 10/1994 |
|---|---|---|
| WO | WO 96/23068 | 8/1996 |
| WO | WO 96/41884 | 12/1996 |
| WO | WO 97/21812 | 6/1997 |
| WO | WO 97/22698 | 6/1997 |
| WO | WO 97/32019 | 9/1997 |
| WO | WO 97/44055 | 11/1997 |
| WO | WO 97/44359 | 11/1997 |
| WO | WO 97/44360 | 11/1997 |
| WO | WO 97/45543 | 12/1997 |

OTHER PUBLICATIONS

Greenberg et al. J. Antimicrobiol Chemotheraphy 2004, vol. 54, pp. 330-340.*
Sista et al. AIDS 2004, vol. 18 (13), pp. 1787-1794, See pp. 1787-1794.*
Wei et al. Antimicrobial agents and chemotheraphy 2002, vol. 46, No. 6, pp. 1896-1905.*
Doranz et al. Cell 1996, vol. 85, pp. 1149-1158.*
Broder et al. Pathology 1996, vol. 64, No. 4, pp. 171-179.*
Feit et al. 2003, J. Pat. Trade. Off. Soc., vol. 85, No. 1, pp. 5-21.*
Moriuchi et al. J. Immunol. 1997, vol. 159, pp. 5441-5449.*
Igarashi et al. Journal of Virol. 2003, vol. 13042-13052.*
Konopka et al. AIDS Research and Human Retroviruses 2002, vol. 18, No. 2, pp. 123-131.*
Chen Yapin et al. J. Virol. 1996, vol. 70, No. 12, pp. 8765-8772.*
Moreno-Altamiano et al. Scani. J. Immunol. 2004, vol. 60, pp. 631-638.*
Chen Yun-Chi et al. J. Virol. 1999, vol. 73, No. 4, pp. 2650-2657.*
Ashorn et al. J. Virol. 64, 2149-2156 (1990).
Bedinger et al. nature 334, 162-165 (1988).
Ben-Baruch et al. J Biol Chem 270(38):22123-8 (1995).
Bullough et al. Nature 371, 37-43 (1994).
Chaudhuri, A., et al. J Biol Chem 269, 7835-8 (1994).
Cheng-Mayer et al. Proc. Natl. Acad. Sci. USA 86, 8575-8579 (1989).
Cocchi, F., et al. Science 720, 1811-1815 (1996) (Cocchi et al.).
Cohen, J. Science 272:809-10, (1996).
Connor, R.I. & Ho, D.D.J. Virol. 68, 4400-4408 (1994).
Connor et al. Virology 206, 936-944 (1995).
Combadiere et al.J Biol Chem 270, 16491-4 (1995).
Cornelissen, M., et al. J. Virol. 69, 1810-1818 (1995).
De Jong et al. J. Virol. 66, 6777-6780 (1992).
Deng et al. (1996) Nature 381:661-6.
Dimitrov, D.S. Nature Medicine 2 640-641 (1996).
Dragic et al. (1996) Nature 381:667-73.

(Continued)

*Primary Examiner*—Bao Qun Li
(74) *Attorney, Agent, or Firm*—Klauber & Jackson

(57) ABSTRACT

Entry of HIV-1 into target cells requires cell surface CD4 as well as additional host cell cofactors. A cofactor required for infection with virus adapted for growth in transformed T cell lines was recently identified and named fusin. Fusin, however, does not promote entry of macrophage-tropic viruses that are believed to be the key pathogenic strains in vivo. It has now been determined that the principal cofactor for entry mediated by the envelope glycoproteins of primary macrophage-tropic strains of HIV-1 is CC-CKR5, a receptor for the β-chemokines RANTES, MIP-1α, and MIP-1β.

1 Claim, 11 Drawing Sheets

OTHER PUBLICATIONS

Figure 1A:
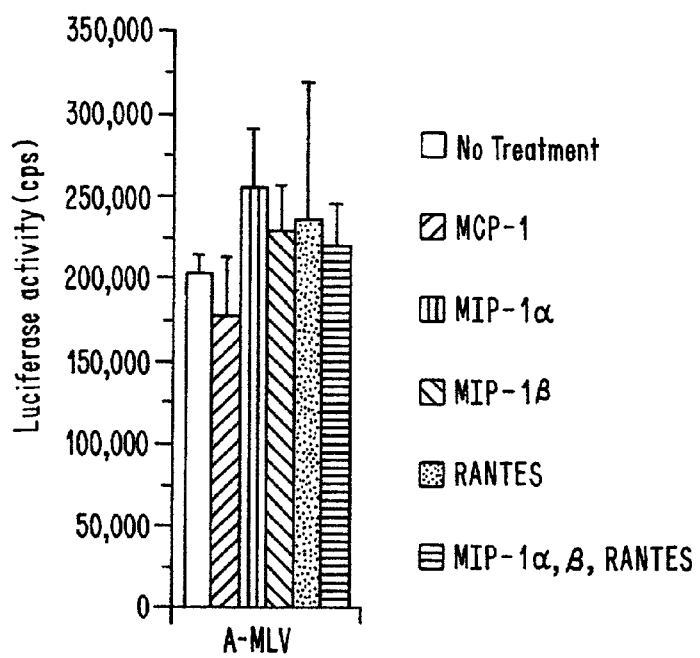

Feng et al. Science 272, 872-877 (1996) (Feng et al.).
Fouchier, R.A., et al. J. Virol. 66, 3183-3187 (1992).
Hanks et al. Science 269, 679-682 (1995).
He, J., et al. J. Virol. 69, 6705-6711 (1995).
Hogan et al. *Manipulating the Mouse Embryo*. Cold Spring Harbor Laboratory Press, Cold Spring Harbor, N.Y. (1986).
Hwang, S.S., Boyle, T.J., Lyerly, H.K. & Cullen, B.R. Science 253:71-4.
Jazin, E.E., et al. Regul. Pept. 47, 247-258 (1993).
Killeen, N., Sawada, S. and Littman, D. R. EMBO 12 1547-1553 (1993).
Koyanagi, Y., et al. Science 236, 819-822 (1987).
Landau, N.R., Warton, M. & Littman, D.R. Nature 334, 159-162 (1988).
Landau, N.R., Page, K.A. & Littman, D.R. J. Virol. 65, 162-169 (1991).
Landau, N.R. & Littman, D.R.J. Virol. 66, 5110-5113 (1992).
Liu et al. J. Virol. 64, 6148-6153 (1990).
Lusso, P., et al. J. Virol. 69, 3712-3720 (1995).
Maddon, P.J., et al. Cell 47, 333-348 (1986).
Morgenstern, J.P. & Land, H. Nucl. Acids Res. 18, 3587-3596 (1990).
Neote et al. Cell 72, 415-25 (1993).
O'Brien, W.A., et al. Nature 348, 69-73 (1990).
Page et al. J. Virol. 64, 5270-5276 (1990).
Paxton, W.A., et al. Nat. Med. 2, 412-417 (1996).
Pear et al. Proc. Natl. Acad. Sci. USA 90, 8392-8396 (1994).
Power, C.A., et al. J Biol Chem 270, 19495-500 (1995).
Samson et al. Biochemistry 35, 3362-3367 (1996).
Sattentau, Q.J. & Weiss, R.A. Cell 52, 631-633 (1988).
Sattentau et al. Virol. 67, 7383-7393 (1993).
Schuitemaker, H., et al. J. Virol. 66, 1354-60 (1992).
Veenstra, J., et al. Clin Infect. Dis. 21, 556-560 (1995).
Westervelt, P., Gendelman, H.E. & Ratner, L. Proc. Natl. Acad. Sci. USA 88, 3097-101 (1991).
Zhu, T., et al. Science 261, 1179-1181 (1993).

\* cited by examiner

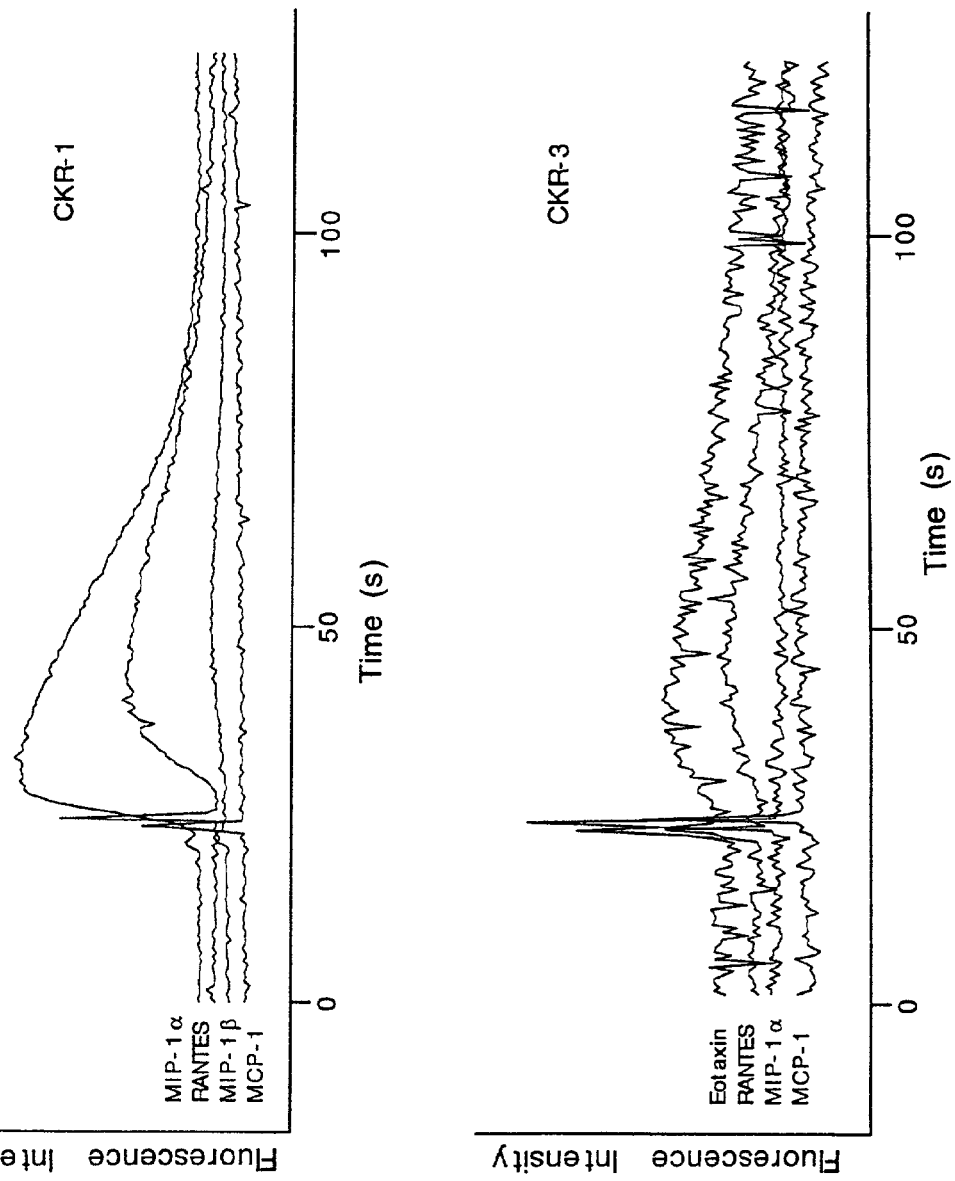

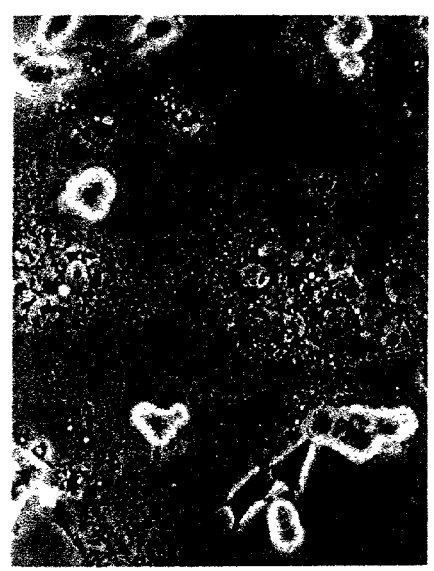
FIG. 4A CKR5 - HXB2
FIG. 4B CKR5 - JRFL
FIG. 4C FUSIN - HXB2
FIG. 4D FUSIN - JRFL

METHODS OF IDENTIFYING G-COUPLE RECEPTORS ASSOCIATED WITH MACROPHAGE-TROPHIC HIV, AND DIAGNOSTIC AND THERAPEUTIC USES THEREOF

CROSS-REFERENCE TO RELATED APPLICATIONS

The present application is a Continuation of application Ser. No. 08/861,105 filed May 21, 1997 now U.S. Pat. No. 6,258,527, which is a Continuation-In-Part of application Ser. No. 08/858,660 filed May 19, 1997, now abandoned, which is based on Provisional Application Ser. No. 60/017,157, filed May 20, 1996, and Provisional Application Ser. No. 60/020,043 filed Jun. 19, 1996. Applicants claim the priority of these Application under 35 U.S.C. §§120 and 119(e). The disclosures of the applications having the Ser. Nos. 08/861,105, 08/858,660 and 60/017,157 are hereby incorporated by reference in their entireties.

The research leading to the present inventions was funded in part by Grant No. AL 3330304 from the National Institutes of Health. The government may have certain rights in the invention.

TECHNICAL FIELD OF THE INVENTION

The present invention relates generally to the infection of target cells by HIV-1, and more particularly to agents identified herein that mediate the entry of macrophage-trophic HIV into such target cells, and to the diagnostic and therapeutic uses to which such agents may be put.

BACKGROUND OF THE INVENTION

The human immunodeficiency viruses infect $CD4^+$ macrophages and T helper cells. Although HIV-1 entry requires cell surface expression of CD4, to which the viral envelope glycoproteins bind, several studies have suggested that it is not sufficient for fusion of the viral envelope to the cellular plasma membrane. Early studies have shown that while human cells expressing a transfected CD4 gene were permissive for virus entry, murine cells expressing human CD4 were not. These findings led to the suggestion that there is a species-specific cell surface cofactor required in addition to CD4 for HIV-1 entry. Subsequent studies have shown that strains of HIV-1 that had been adapted for growth in transformed T-cell lines (T-tropic strains) could not infect primary monocytes or macrophages; in contrast, primary viral strains were found to infect monocytes and macrophages, but not transformed T cell lines. This difference in tropism was found to be a consequence of specific sequence differences in the gp120 subunit of the envelope glycoprotein, suggesting that multiple cell type-specific cofactors may be required for entry in addition to CD4.

The nature of the cofactors required for HIV entry proved elusive until the recent identification by Feng et al. of fusin, a member of the seven transmembrane G-protein coupled receptor family. Fusin (CXCR-4) was shown to act as a co-receptor for T-tropic strains; however, it did not support infection of $CD4^+$ cells by macrophage-tropic viruses, which more closely resemble those that predominate in infected individuals throughout the course of the disease, particularly in the asymptomatic phase. In addition, these strains appear to be responsible for HIV-1 transmission, both sexually and by transfer of infected blood. Rare individuals who are resistant to sexual transmission of HIV-1 have T-cells that are readily infected by T-tropic virus, but cannot be infected by macrophage-tropic virus, further supporting a role for macrophage-tropic virus in sexual transmission of HIV-1.

Cocchi et al. recently characterized inhibitors of HIV-1 replication present in supernatants of $CD8^+$ T cells as the β-chemokines RANTES, MIP-1α and MIP-1β. Chemokines are chemotactic cytokines that are released by a wide variety of cells to attract macrophages, T cells, eosinophils, basophils and neutrophils to sites of inflammation (reviewed in ref. 14). The chemokines fall into two classes, C—X—C (α) and C—C (β), depending on whether the first two cysteines are separated by a single amino acid or are adjacent. The α-chemokines such as IL-8, NAP-2 and MGSA are chemotactic primarily for neutrophils, while β-chemokines such as RANTES, MIP-1α, MIP-1β, MCP-1, MCP-2, and MCP-3 are chemotactic for macrophages, T-cells, eosinophils and basophils. The chemokines bind specific cell surface receptors belonging to the family of G protein-coupled seven transmembrane domain proteins (reviewed in Ref. 15). Upon binding their cognate ligands, chemokine receptors transduce an intracellular signal through the associated trimeric G protein. This results in a rapid increase in intracellular calcium concentration. There are at least seven human chemokine receptors that bind or respond to β-chemokines with the following characteristic pattern: CC-CKR1 (MIP-1α, MIP-1β, MCP-3, RANTES), CC-CKR-2A and CC-CKR-2B (MCP-1, MCP-3), CC-CKR-3 (eotaxin, RANTES, MCP-3), CC-CKR-4 (MIP-1α, RANTES, MCP-1), CC-CKR-5 (MIP-1α, RANTES, MIP-1β), and the Duffy blood group antigen (RANTES, MCP-1). These transmembrane receptors could be involved in HIV infection.

Therefore, there is a need to identify a translocation promoting agent that functions in conjunction with CD4 during HIV infection in macrophage. Further, there is a need to provide methods for identifying drugs that can interfere with HIV infection of macrophage by hindering the interaction of CD4, the translocation promoting agent and HIV envelope proteins.

SUMMARY OF THE INVENTION

In its broadest aspect, the present invention relates to the identification and application of an agent capable of promoting the translocation of macrophage-trophic HIV through the membrane of a target $CD4^+$ cell, which agent exhibits certain of the following characteristics and activities:

A. It is present in, on, or proximal to the cell membrane of the target $CD4^+$ cell;

B. It acts in tandem with CD4, in connection with the translocation; and

C. It is capable of interacting with associated G-proteins to thereby transduce an intracellular signal.

A further characteristic attendant to the activity of the translocation promoting agent of the present invention is an observed increase in the concentration of intracellular calcium. The present agent may also be described as a mediator of the entry of envelope glycoproteins of macrophage-trophic strains of HIV-1 into target cells.

In a further aspect of the invention, the present translocation promoting agent appears to act in conjunction with CD4 in facilitating the penetration of the macrophage-trophic virus into the target cell to establish HIV infection. A particular family of receptors known as C—C (or β) chemokine receptors (CKRs) has been identified as defining certain of the activities and characteristics set forth above, and a specific such receptor, CC-CKR5, is exemplified herein.

Other analogous receptors, such as those encoded by some viruses, particularly members of the Herpes virus family (CMV, HHV-6, HHV-8), serve to broaden the host range of HIV in individuals infected with both HIV and these viruses. This may therefore increase the range of tissues infected or provide a ligand for HIV envelope that may result in deleterious signal transduction in various tissues. Such information could lead to novel approaches to block the synergy between HIV and viral cofactors.

The present invention also relates to the use of a recombinant DNA molecule or cloned gene, or a truncated or degenerate variant thereof, which encodes a translocation promoting agent or the active portion thereof; preferably a nucleic acid molecule, in particular a recombinant DNA molecule or cloned gene. In another embodiment, the human and murine DNA sequences of the translocation promoting agent of the present invention, or portions thereof, may be prepared as probes to screen for complementary sequences and genomic clones in the same or alternate species. The present invention extends to probes so prepared that may be provided for screening cDNA and genomic libraries for the translocation promoting agent. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences so prepared or constituted. Correspondingly, the preparation of antisense RNA and ribozymes are included herein.

The present invention also includes translocation promoter agents having the activities noted herein. In a further embodiment of the invention, the full DNA sequence of the recombinant DNA molecule or cloned gene so determined may be operatively linked to an expression control sequence which may be introduced into an appropriate host. The invention accordingly extends to unicellular hosts transformed with the cloned gene or recombinant DNA molecule comprising a DNA sequence encoding the present translocation promoter agent(s).

According to other preferred features of certain preferred embodiments of the present invention, a recombinant expression system is provided to produce biologically active animal or human translocation promoter agent.

The present invention also includes animal models. In one aspect of the invention a non-human animal model is used in the study of HIV infection and HIV disease in order to develop modes of diagnosis, prevention, treatment and/or cures. In some embodiments, a transgenic animal is produced containing the CD4 enhancer/promoter/silencer and the CD4 coding sequence as described by Killeen et al., The EMBO J. 12, 1547–1553 (1993) along with a translocation promoting agent. In one such embodiment, a transgenic animal has a translocation promoting agent regulated by the CD4 enhancer/promoter/silencer. More particularly, the regulation of the translocation promoting agent may include the CD4 enhancer/promoter/silencer plus a macrophage-specific enhancer. Yet further, the macrophage-specific enhancer can be all or a functional portion of the first intron of the human CD4 gene.

In a further aspect of the invention, a transgenic non-human animal is produced with the gene for the animal homolog of the translocation promoting agent replaced by its human counterpart. In this embodiment, the translocation promoting agent may be selected from CC-CKR-5, fusin, CC-CKR-2B and CC-CKR-3. In a preferred embodiment the translocation promoting agent is CC-CKR-5.

In a variant embodiment, a transgenic animal is produced with the genes for two such animal homologs of two translocation promoting agents replaced by their human counterparts. In one such specific embodiment, one of the translocation promoting agents is CC-CKR-5 and the other is fusin. In other embodiments more than two such animal homologs are replaced by their human counterparts. In a more preferred embodiment the transgenic animal also contains human CD4.

In a more generalized application of this aspect of the invention the replacement of the animal homolog gene is performed in the animal germ line. Preferably as a knockin as generally described in Hanks et al., (1995). A more focussed construct may be prepared by the replacement of the gene in T-cells and macrophages. In variant preparations, human CD4 may also be present in the animal T-cells and/or macrophages. A particular replacement gene that may be used comprises a nucleic acid that encodes a human translocation promoting agent expressed under the control of a gene naturally expressed in macrophages and/or T-Cells e.g. lysozyme. In a specific embodiment, the human translocation promoting agent placed between the 5' end and the 3' prime end of the lysozyme gene is CC-CKR-5.

The non-human animal prepared in accordance herewith may be any animal that is amenable to transgenic technology. In a preferred embodiment the non-human animal is selected from the group consisting of a mouse, a rabbit, a sheep, a goat, and a pig. In another preferred embodiment, the non-human animal is a primate.

The concept of the translocation promoter agent contemplates that specific factors exist for correspondingly specific ligands, such as CD4 and the like, as described earlier. Accordingly, the exact structure of each translocation promoter agent will understandably vary so as to achieve this ligand and activity specificity. It is this specificity and the direct involvement of the translocation promoting agent in the chain of events leading to HIV infection, that offers the promise of a broad spectrum of diagnostic and therapeutic utilities.

In a related aspect, the mutability of retroviruses in general, and specifically HIV-1, is consistent with the identity of the translocation promoting agent changing as the viral infection progresses. Such changes are due to changes in HIV-1 that lead to the emergence and activity of different translocation promoting agents in different populations (e.g. geographically separated groups of people.) Furthermore, changes in the virus and its choice of translocation promoting agent can be indicative of different stages of the infection in an infected individual. Information regarding the progression of the infection is extremely valuable to that individual and their health care provider, e.g., such as in the treatment of that individual.

The present invention includes a method of monitoring the progression of the HIV infection by determining the identity of the translocation promoting agent as the infection progresses. The method includes the use of the assorted cell lines disclosed herein (and others prepared in the same manner) which express the different β-chemokine receptors along with CD4. β-Chemokine receptors are prime candidates for being translocation promoting agent agents.

The first step entails quantifying the amounts of the particular translocation promoting agents that are utilized by the virus during the specific stages of the infection, in a relevant population of HIV-1 infected people. A proportional relationship between these quantified amounts may then be correlated with the specific stages of HIV-1 infection. The second step is to quantify the amounts of the particular translocation promoting agents that are utilized by the virus in a biological sample obtained from an infected individual. The third step is to correlate the proportions determined for the individual with those determined for the group and thereby determine the stage of the HIV-1 infection for the individual.

The amount of each β-chemokine used as a translocation promoting agent by HIV-1 in a given biological sample can be determined with the assorted cell lines disclosed herein. These cell lines express different β-chemokine receptors along with CD4 and may be detectably labeled so as to allow their relative sensitivity to the virus be determined. Only the HIV-1 strain that uses the particular β-chemokine as the translocation promoting agent, can successfully infect a test cell with that particular β-chemokine. A detectable label inside the cell that is activated by successful infection will allow quantitation of the amount of the particular β-chemokine. Detectable labels may be either a genetic marker or linked to a genetic marker that is only expressed upon HIV-1 infection. Appropriate detectable labels include luciferase green fluorescent protein, as well as the others described herein.

The invention also includes an assay system for the screening of potential drugs effective to modulate translocation of macrophage-trophic HIV into target mammalian cells by interrupting or potentiating the translocation promoting agent. In one instance. the test, drug could be administered to a cell (such as a transformal cell) with the ligand that activates the translocation promoting agent, or an extract containing the activated translocation promoting agent, to determine its effect upon the binding activity of the translocation promoting agent to any chemical sample (including DNA), or to the test drug, by comparison with a control.

The assay system could more importantly, be adapted to identify drugs or other entities that are capable of binding to the translocation promoting agent and/or to corresponding factors or proteins, either in the cytoplasm or in the nucleus, and inhibit or potentiate the translocation promoting activity. Such an assay would be useful in the development of drugs that would be specific against particular cellular activity, or that would potentiate such activity, in time or in level of activity. For example, such drugs might be used to inhibit penetration of HIV into the target cell, or to treat other pathologies.

One embodiment includes an in vitro method for identifying a viral envelope glycoprotein that binds to a particular translocation promoting agent comprising contacting a labeled viral envelope glycoprotein with a translocation promoting agent attached to a solid support, washing the solid support, and then detecting the labeled viral envelope glycoproteins associated with the solid support. A viral envelope glycoprotein that binds the translocation promoting agent is identified when the labeled viral envelope glycoprotein is detected associated with the solid support. Any translocation promoting agent of the present invention may be used in this assay. In a related embodiment, the cytoplasmic domain of a translocation promoting agent is attached to the solid support rather than the full length protein. In one embodiment, the viral envelope glycoprotein is an HIV envelope glycoprotein. In a preferred embodiment the translocation promoting agent is CC-CKR5.

In yet a further embodiment, the invention contemplates the identification and use of antagonists of the activity of a translocation promoting agent. In particular, an agent or molecule that inhibits the HIV-translocating activity of the translocation promoting agent. In a specific embodiment, the antagonist can be a peptide having the sequence of a portion of the active domain of the translocation promoting agent.

The utility of the present invention extends to the use of the present invention in assays to screen for drugs and small molecules that would function as inhibitors of translocation promoting agent activity. A particular such assay may be constituted in a transgenic non-human mammal that comprises a DNA construct containing a human CD4 gene and a DNA construct containing human CC-CKR-5 gene, wherein both CD4 protein and CC-CKR-5 protein are expressed by said non-human mammal.

The reporter gene can encode any detectable gene product but is more preferably either luciferase, or green fluorescent protein. The HIV LTR is preferably HIV-2 LTR. The human chemokine receptor is preferably CC-CKR1, CC-CKR2A, CC-CKR2B, CC-CKR-3, CC-CKR-4, CXC-CR4, or CC-CKR5.

The present invention also includes a method of using such a cell for identifying a human chemokine receptor that facilitates the infection of a particular HIV strain into the transformed mammalian cell. One embodiment of this type comprises infecting the cell with a primary HIV strain, and then detecting the reporter gene. The human chemokine receptor is identified when the reporter gene is detected above the background value determined in the absence of HIV infection. In one embodiment the reporter gene encodes green fluorescent protein. In one particular embodiment of this type, the detecting is performed by FACS analysis. The human chemokine receptor is preferably CC-CKR1, CC-CKR2A, CC-CKR2B, CC-CKR-3, CC-CKR-4, CC-CKR5 or CXC-CR4. The particular HIV strain is a preferably a primary HIV-1 strain.

The present invention also includes a method of using such cells for identifying a drug that interferes with the translocation of HIV. One such embodiment comprises administering a potential drug to the cell; infecting the cell with a primary HIV strain; and then detecting the reporter gene. In this case, the reporter gene is detected in the absence of the drug, indicating that the HIV strain is translocated into the cell. A potential drug is identified as a drug when the reporter gene is either not detected, or is detected in a lesser amount in the presence of the drug. In one embodiment, the reporter gene encodes green fluorescent protein. In one particular embodiment of this type, the detecting is performed by FACS analysis. The human chemokine receptors are preferably CC-CKR1, CC-CKR2A, CC-CKR2B, CC-CKR-3, CC-CKR-4. CC-CKR5, and CXC-CR4.

The present invention also includes a method of using such cells for identifying an antibody that interferes with the translocation of HIV into the cell. One embodiment comprises administering an antibody to the cell; infecting the cell with a primary HIV strain; and then detecting the reporter gene. The reporter gene is detected in the absence of the antibody, indicating that the HIV strain is translocated into the cell. The potential antibody is identified as an antibody that interferes with the translocation of HIV, when the reporter gene is either not detected, or is detected in a lesser amount in the presence of the antibody. The antibody can be an antibody to HIV, an antibody to CD4, an antibody to the translocation promoting agent, an antibody to a purified HIV envelope protein, or an antibody raised specifically against a complex of two or more the above. In one such embodiment the reporter gene encodes green fluorescent protein. In a particular embodiment of this type, the detecting is performed by FACS analysis. The human chemokine receptor is preferably CC-CKR1, CC-CKR2A, CC-CKR2B, CC-CKR-3, CC-CKR-4, CC-CKR-5, or CXC-CR4.

The present invention likewise extends to the development of antibodies to the translocation promoting agent(s), including naturally raised and recombinantly prepared antibodies. Antibodies can be used for various purposes including to evaluate the relative resistance or permissiveness of $CD4^+$ cells to HIV infection to block HIV translocation, and to identify such proteins that function as macrophage-tropic HIV translocation receptors. For example, the antibodies could be used to screen expression libraries to obtain the gene or genes that encode the translocation promoting agent(s). Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating translocation promoting agent activity.

In a specific embodiment, an antibody is raised against CC-CKR-5 and inhibits HIV binding. Such an antibody may be used for permissive immunotherapy and protects against host cell invasion by a number of viral isolates. Such an antibody was raised against fusin and has been shown to inhibit HIV-1 infection [see Dimitrov, D. S. Nature Medicine 2 640–641 (1996)].

In another embodiment, the antibody is specific for a conformational epitope on the translocation promoting agent that becomes accessible upon binding CD4 and/or an envelope protein of HIV-1. In still another embodiment, the antibody reacts with a shared epitope of the translocation promoting agent and HIV or CD4 or both. In preferred embodiments of this aspect of the invention the translocation promoting agent is CC-CKR-5. In yet another embodiment, a chimeric antibody is prepared that specifically binds to the gp120-gp41 molecules of HIV-1 and CC-CKR-5.

The present invention also includes chimeric proteins containing the translocation promoting agent and an additional protein or peptide. In one such chimeric protein, the translocation promoting agent includes an epitope tag inserted into its amino-terminal extracellular domain. The chimeric protein can be encoded by a translocation promoting agent expression vector. In a preferred embodiment of this type, the chimeric protein is expressed in a mammalian cell as a transmembrane receptor which can be detected with an antibody that recognizes the epitope tag.

In one such embodiment the translocation promoting agent contains an influenza (HA) epitope tag in its N-terminal extracellular domain. In an embodiment of this type the HA epitope tag is a peptide having an amino acid sequence of SEQ ID NO:10 or SEQ ID NO:12. In a related embodiment, the N-terminal DNA sequence of the HA epitope tag comprises SEQ ID NO:9 or SEQ ID NO:11. In one particular embodiment, the translocation promoting agent is CC-CKR5. In a preferred embodiment of this type, the insertion of the HA epitope tag also allows for very sensitive detection of the translocation promoting agent at the cell surface with the use of an anti-HA monoclonal antibody. In a specific embodiment of this type, the amino-terminal amino acid sequence of the chimeric protein comprises SEQ ID NO: 6. In a related embodiment, the N-terminal DNA sequence of the chimeric protein comprises SEQ ID NO:5.

Thus, the translocation promoting agent(s), analogs, thereof, and any antagonists or antibodies that may be raised thereto, are capable of use in connection with various diagnostic techniques, including immunoassays. Such a radioimmunoassay, for example, can use an antibody to the translocation promoting agent that has been labeled by either radioactive addition, or radioiodination.

In an immunoassay, a control quantity of a solubilized translocation promoting agent or antibodies thereto, or the like may be prepared and may then be introduced into a cellular sample. After the labeled material or its binding partner(s) has had an opportunity to react with sites within the sample, the resulting mass may be examined by known techniques, which may vary with the nature of the label attached.

The present invention includes an assay system which may be prepared in the form of a test kit for the quantitative analysis of the extent of the presence of the translocation promoting agent, or to identify drugs or other agents that may mimic or block their activity. The system or test kit may comprise a labeled component prepared by one of the radioactive and/or enzymatic techniques discussed herein, coupling a label to the translocation promoting agent, their agonists and/or antagonists, and one or more additional immunochemical reagents, at least one of which is a free or immobilized ligand, capable either of binding with the labeled component, its binding partner, one of the components to be determined or their binding partner(s).

In a further embodiment, the present invention relates to certain therapeutic methods which would be based upon the activity of the translocation promoting agent(s), its (or their) subunits, or active fragments thereof, or upon agents or other drugs determined to possess the same activity. A first therapeutic method is associated with the prevention of the manifestations of conditions causally related to or following from the binding activity of the translocation promoting agent or its subunits, and comprises administering an agent capable of modulating the production and/or activity of the translocation promoting agent or subunits thereof, either individually or in mixture with each other in an amount effective to prevent the development of those conditions in the host. For example, drugs or other binding partners to the translocation promoting agent or proteins may be administered to inhibit or potentiate translocation promoting agent activity.

More specifically, such therapeutic methods could include the method for the treatment of various pathologies or other cellular dysfunctions and derangements by the administration of pharmaceutical compositions that may comprise effective inhibitors or enhancers of the HIV translocating promoter activity of the translocation promoting agent or its subunits, such as antibodies, or other drugs developed for instance by a drug screening assay prepared and used in accordance with a further aspect of the present invention. For example, drugs, antibodies or other binding partners to proteins such as CC-CKR5, may be administered to inhibit the activity of the translocation promoting agent. Particular agents contemplated herein include proteins such as CC-CKR5 modified by the binding of the extracytoplasmic domain to a nonfunctional transmembrane domain, or to a lipid, to serve as a competitive inhibitor. Such modified translocation promoting agents may be inserted into macrophages by gene therapy techniques and placed into subject animals, including humans to prevent HIV infection or combat HIV infection at its early stage of infection.

Further, the invention extends to the soluble form(s) of the translocation promoting agent, that may function in similar fashion to antagonists to the agent, to inhibit HIV ingress to the target cell. All of the aforementioned agents, including small molecules and other cognates, may be formulated for use in the treatment of fluids such as the blood, and in the preparation, for example, of a spermicidal composition or like formulation, to treat the development of macrophage-trophic HIV that is known to be present in infected blood samples, and that is particularly known to be sexually transmitted.

In particular, proteins corresponding to translocation promoter agents, such as, for example, the chemokine receptors set forth herein, their antibodies, agonists. antagonists, or active fragments thereof, could be prepared in pharmaceutical formulations for administration in instances wherein inhibitory therapy is appropriate. The application of the therapeutic compositions and methods of the invention will, it is believed, dramatically reduce the incidence of primary HIV infection.

Yet another aspect of the invention includes the identification of a ligand for fusin. Supernatents and extracts of various cell lines and populations (e.g. CD8-lineage cells) are used to assay for the inhibition of infection by a fusin-tropic virus.

In a related aspect the identified ligand for fusin is isolated by standard column chromatography and gel electrophoresis, with the use of the assay described above. In one embodiment of this aspect of the invention, a fusin affinity column is used.

Accordingly, it is a principal object of the present invention to provide antagonists including antibodies, to the translocation promoter agent and its subunits, and methods for their preparation, including recombinant means.

It is a further object of the present invention to provide a method for detecting the presence of the translocation promoter agent and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of the translocation promoter agent and/or its subunits in mammals.

It is a still further object of the present invention to provide a method for the treatment of mammals to control the amount or activity of the translocation promoter agent or subunits thereof, so as to alter the adverse consequences of such presence or activity, or where beneficial, to enhance such activity.

It is a still further object of the present invention to provide a method for the treatment of mammals to control the amount or activity of the translocation promoter agent or its subunits, so as to treat or avert the adverse consequences of invasive, spontaneous or idiopathic pathological states.

It is a still further object of the present invention to provide pharmaceutical compositions for use in therapeutic methods which comprise or are based upon the translocation promoter agent, its subunits, their binding partner(s), or upon agents or drugs that control the production, or that mimic or antagonize the activities of the translocation promoter agent.

Other objects and advantages will become apparent to those skilled in the art from a review of the ensuing description which proceeds with reference to the following illustrative drawings.

BRIEF DESCRIPTION OF THE DRAWING FIGURES

Figure 1B:
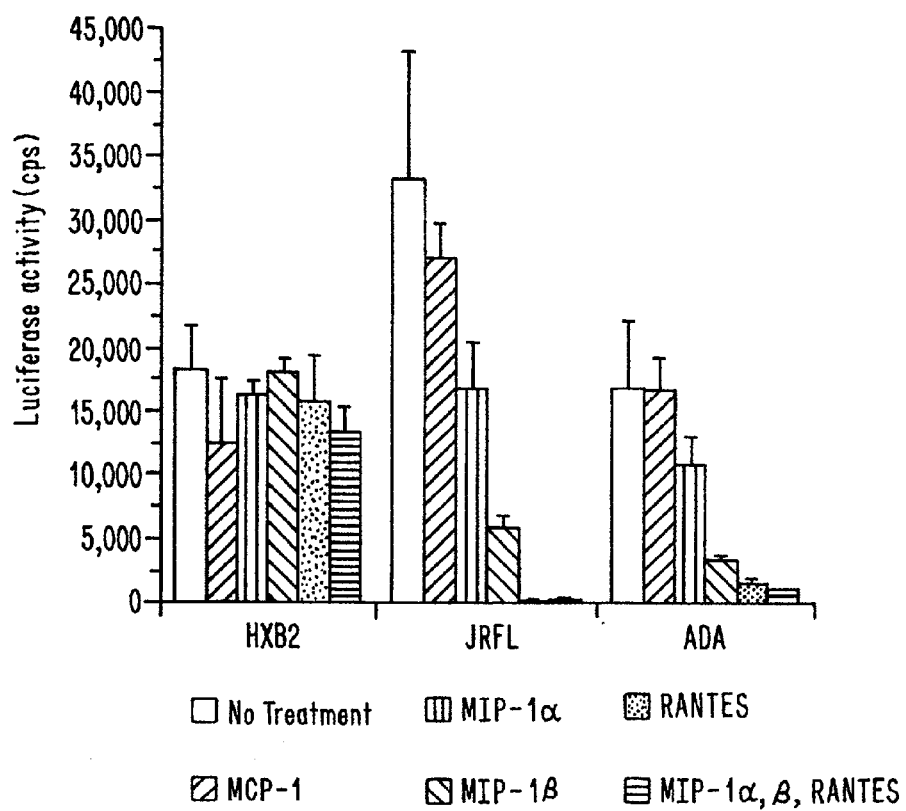

FIG. 1A-1B show graphs indicating that chemokines block infection at the level of viral entry PM1 cells infected with luciferase reporter viruses pseudotyped with HIV-1 macrophage-tropic (ADA, JRFL) or T-cell line adapted virus (HXB2) Envs FIG. 1B or A-MLV Env FIG. 1A in the presence or absence of a mixture of individual β-chemokines or a mix. Luciferase activity was measured four days later as described below. This experiment was repeated four times with similar results.

Figure 2A:
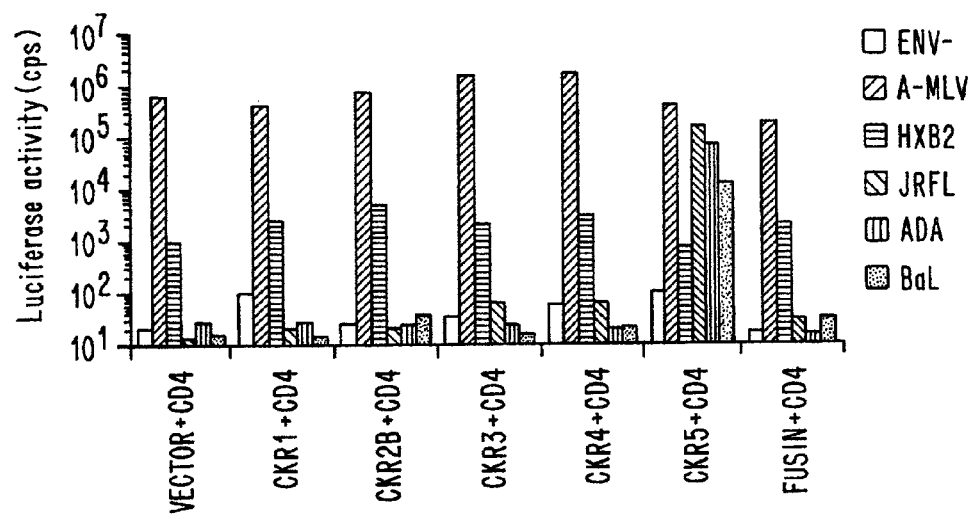
Figure 2B:
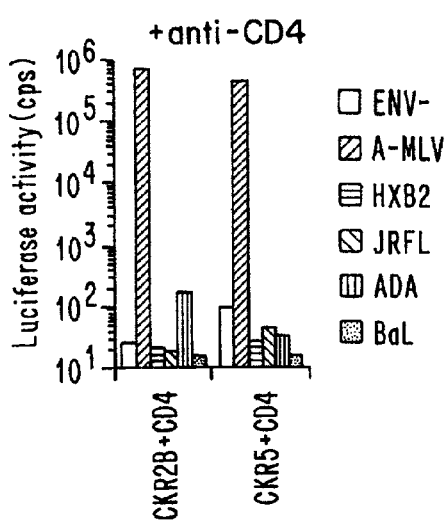
Figure 2C:
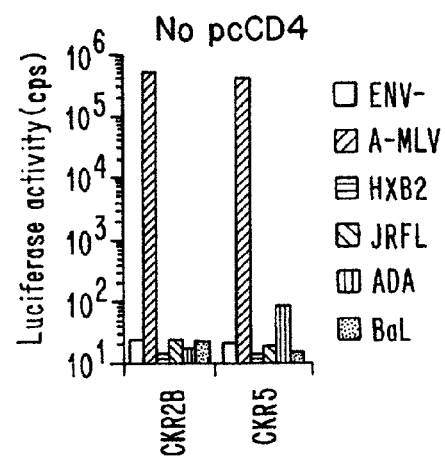

FIG. 2A-2B show graphs which illustrate that CC-CKR5 mediates entry of macrophage-tropic HIV-1. cDNAs encoding chemokine receptors 1, 2A, 2B, 3, 4 and 5 were amplified from activated PBMC RNA using primers hybridizing to the respective 5' and 3' untranslated regions. Amplified products were cloned into pcDNA-I (InVitrogen) and pBABE-puro expression vectors. Each of the cDNAs was sequenced and determined to correspond to that previously reported. FIG. 2A, depicts 293 cells that were transfected with 5 μg CD4 expression vector pcCD4 and 15 μg pcDNA-I expression vectors for each of the CC-CKR genes. The next day the cells were plated in 24 well dishes ($2\times10^4$ per well) and one day later were infected with 20 ng p24 luciferase reporter viruses in a volume of 300 μl. Four days later, luciferase activity was measured as described above. FIG. 2B is the same as in FIG. 2A with addition of 20 μg ml$^{-1}$ Leu3A 30 min before adding virus. FIG. 2C is the same as FIG. 2A, except that pcCD4 was omitted from the transfection and replaced by pcDNA-1 control vector DNA.

Figure 3A:
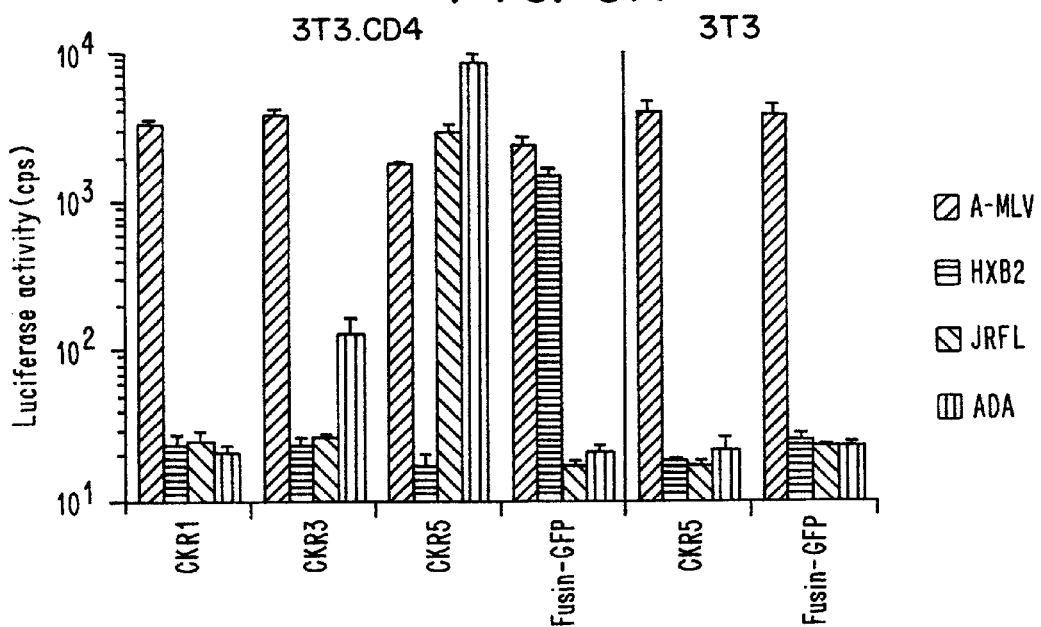
Figure 3B:
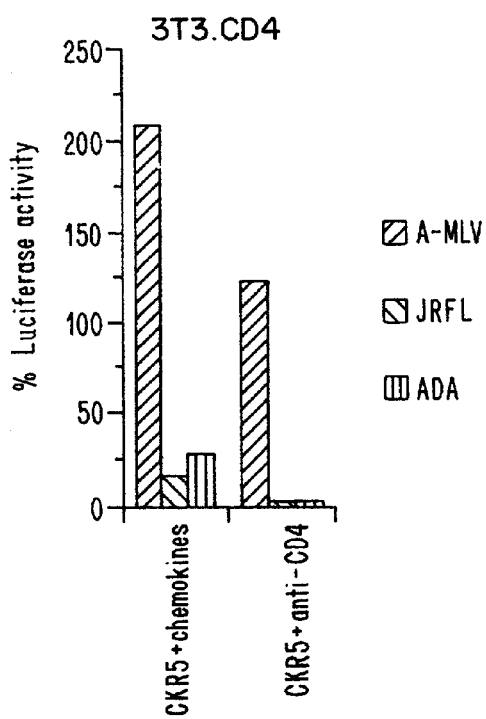
Figure 3C:
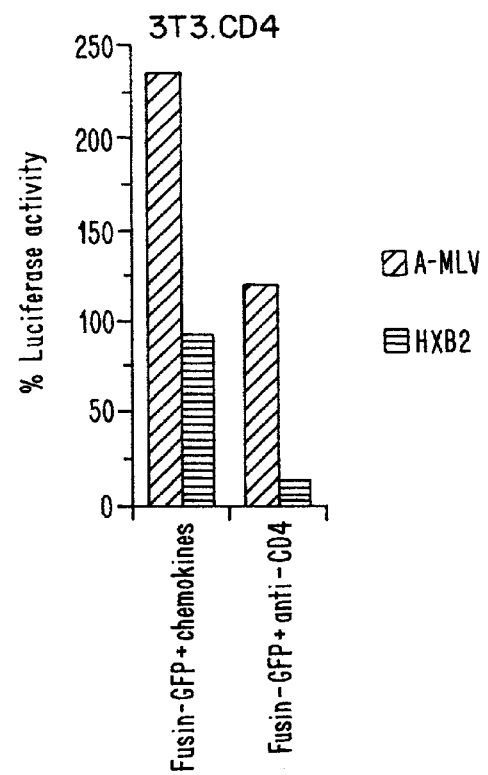
Figures 3D, 3E:
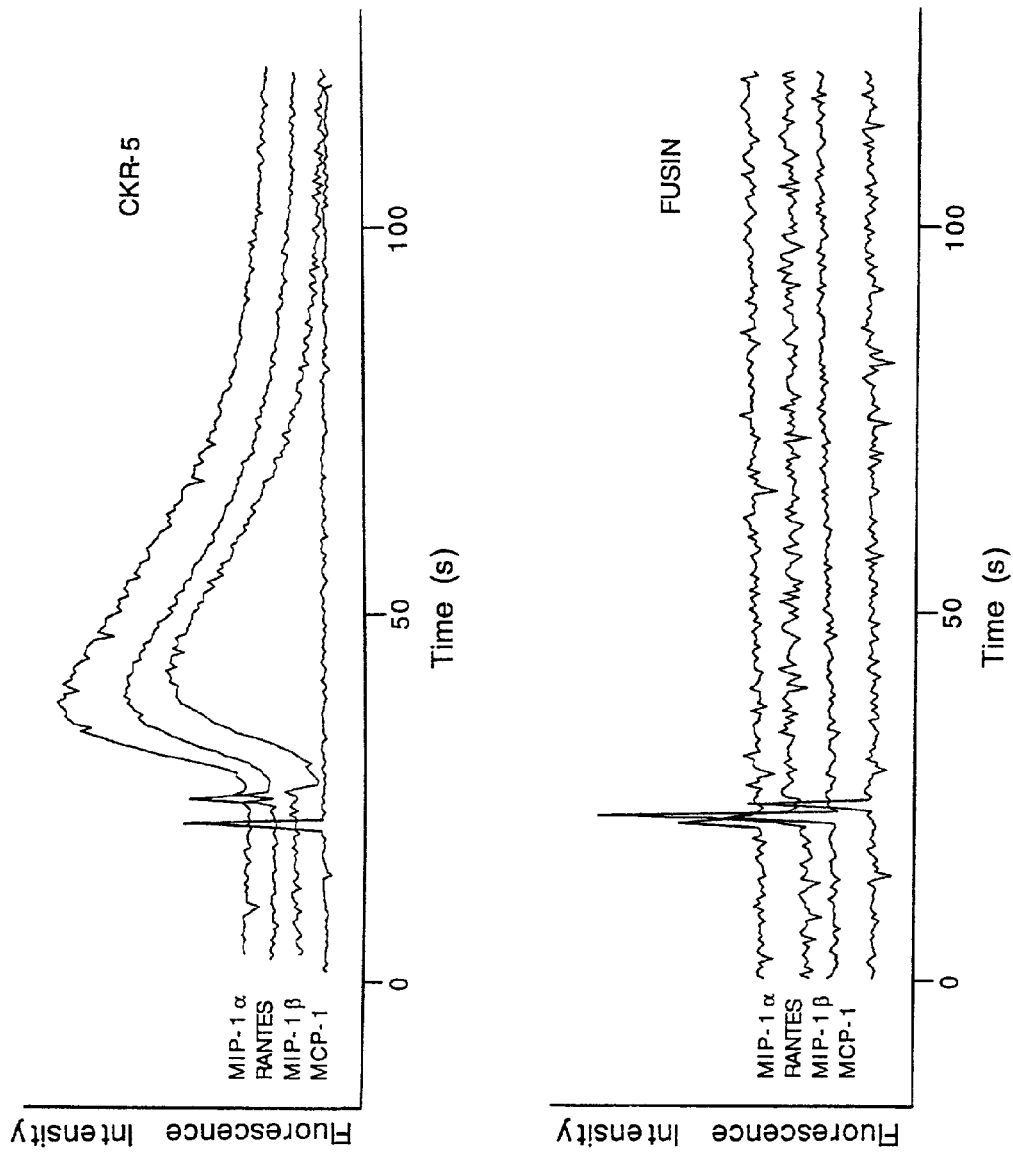
Figure 3H:
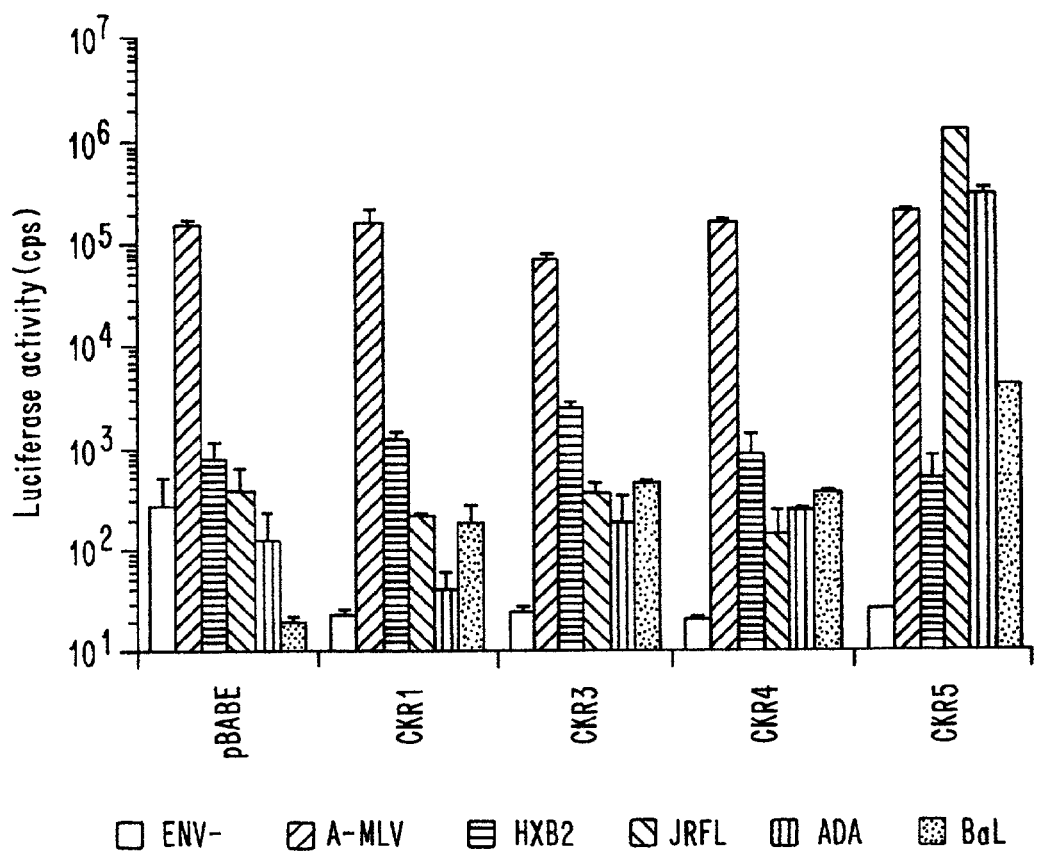
Figure 3I:
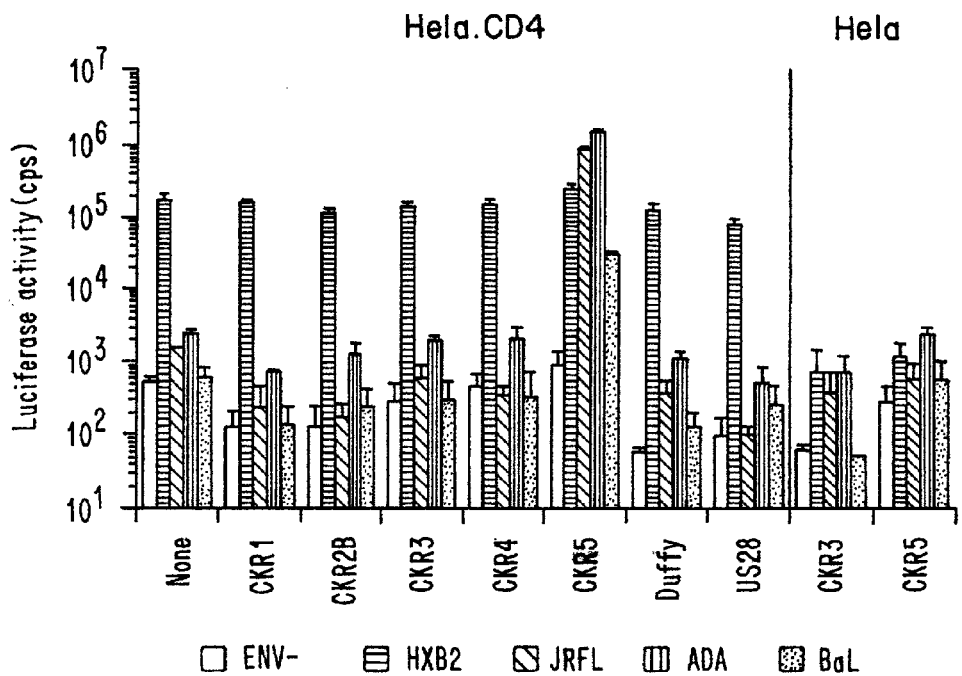
Figure 3J:
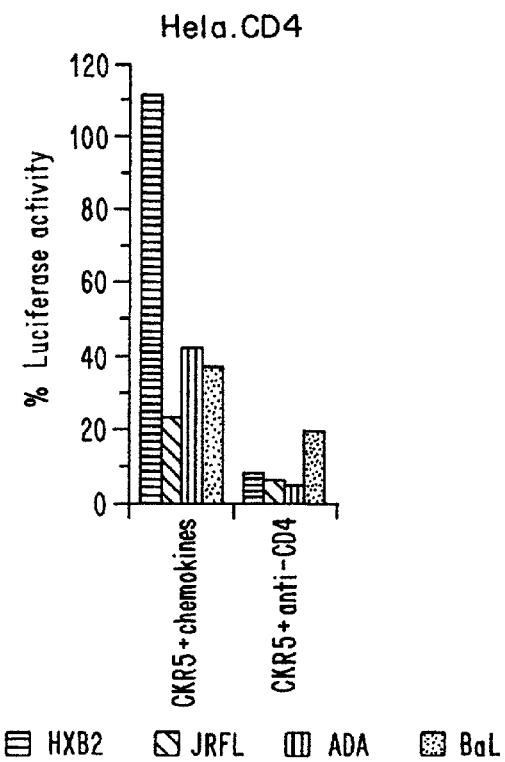

FIGS. 3a–3j show graphs which illustrate that stable expression of CKR5 confers susceptibility to HIV entry that can be inhibited by anti-CD4 mAb or chemokines. Candidate receptors were introduced into CD4-positive and CD4-negative cell lines. FIGS. 3a–3c illustrate the infection of NIH3T3.CD4 cells (murine fibroblast) expressing different chemokine receptors or fusion-GFP. Fusion-GFP is a fusion protein in which Green Fluorescent Protein (GFP) has been attached to the C-terminus of fusion. In the lower panels, (FIGS. 3b–3c), β-chemokine and anti-CDO4 blocking are expressed as a percentage of luciferase activity in the presence of blocking agent as compared to untreated controls. FIGS. 3d–3g show the chemokine induction of $Ca^{2+}$ signaling in 3T3.CD4-CKR stable transfectants. Comparison of cytoplasmic $C^{2+}$ levels in 3T3 cells expressing recombinant C—C chemokine receptors-1, -3, -5 (CKR-1, CKR-3, CKR-5), and the orphan receptor fusion after challenge with various chemokines as listed. Chemokines were added through an injection port at approximately 20 seconds (the sharp spike in each record) to a final concentration of 100 nM. The rise in intracellular calcium is represented by the rapid increase in relative fluorescence intensity. FIG. 3h shows the infection of HOS.CD4 cells (human osteosarcoma). FIG. 3i-3j shows the infection of Hela.CD4 (human carcinoma); US28 is a -chemokine receptor encoded by human cytomegalovirus. Duffy antigen is a promiscuous chemokine receptor expressed primarily on erythroid cells.

FIG. 4A-4D illustrate that CC-CKR-5 mediates Env-dependent fusion. 293T cells were transfected with equal amounts of pcDNA1-based Env and pcRev expression vectors. Two days later the transfected cells ($1.5\times10^5$) were seeded with 3T3-T4-CKR5 or 3T3-T4-fusin ($3.0\times10^5$) cells. The next day the cells were stained with Giemsa stain. Syncytia were counted and plates were photographed.

Figure 5A:
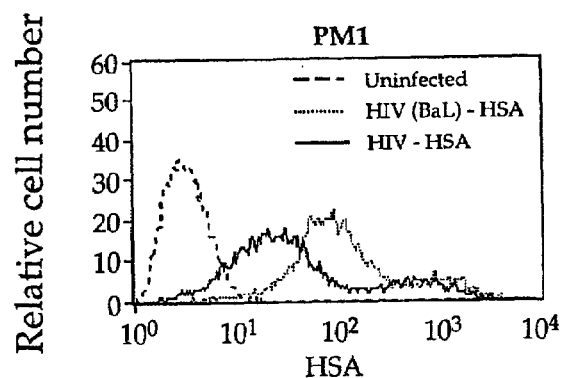
Figure 5B:
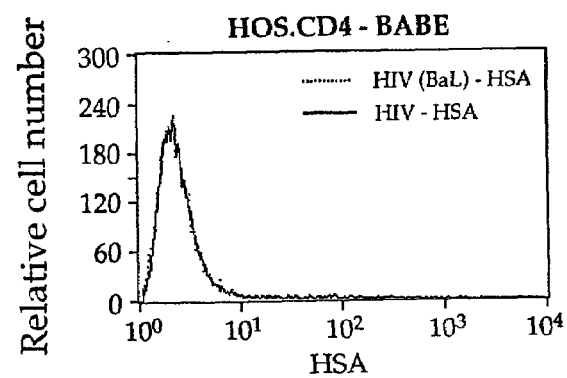
Figure 5C:
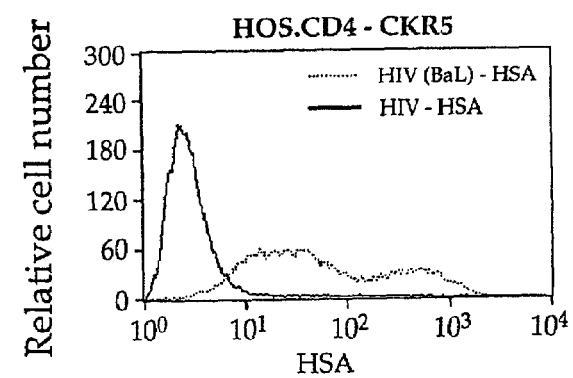
Figure 5D:
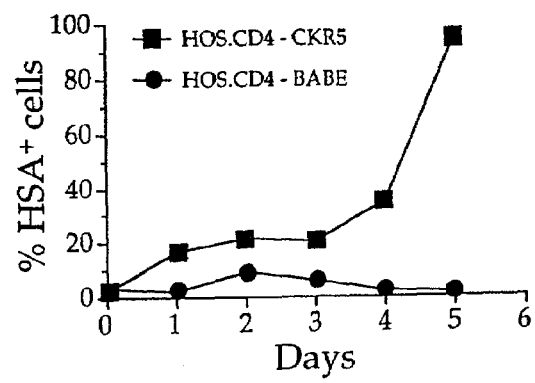

FIG. 5A-5D are graphs showing that CKR5 supports macrophage-tropic, but not T-cell line adapted virus replication in human and murine cells. FIG. 5A–5C depicts the results when PM1, HOS-T4-BABE and HOS-T4-CKR5 cells ($5\times10^5$) which were plated in 6-well dishes and the next day infected with replication competent T-cell line adapted HIV-HSA or macrophage-tropic HIV(BAL)-HSA reporter viruses (50 ng p24). HIV-HSA is based on the T-cell line adapted virus pNL4-3, but contains, in place of nef, the gene encoding the small cell surface protein, heat stable antigen (HSA or CD24). HIV(BAL)-HSA virus is similar except that its env gene has been replaced by the Sal-I-Bam-HI restriction fragment containing the macrophage-tropic Env of BaL. HIV(BaL)HSA replicates in PM1 cells but not in CEM cells, while HIV(HSA) replicates in both cell types. Both viruses show a characteristic bimodal distribution of HSA staining cells. This is likely to reflect whether the cells are in the early or late phase of the replication cycle. After five days the cells were stained with FITC-conjugated anti-HSA monoclonal antibody (Pharmingen) and analyzed in a Becton-Dickenson FACScaliber. FIG. 5D shows the time course of HIV(BaL) HSA virus replicating on HOS-T4-CKR5 cells. Cells were infected with HIV(BaL)HSA and analyzed by FACS on indicated days.

Figure 6:
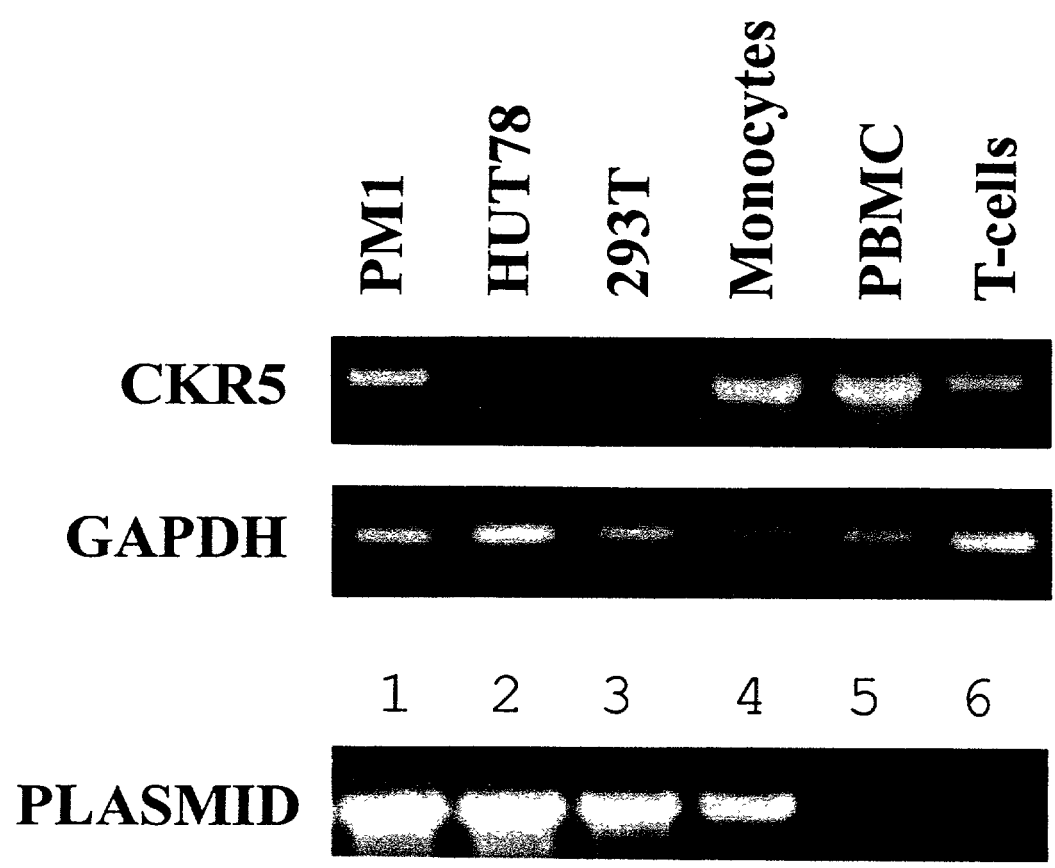

FIG. 6 is a gel showing that CC-CKR-5 is expressed in T cells and monocyte/macrophages. Total RNA was prepared from the indicated cell-types using Triazol reagent (Gibco/BRL), treated with RNase-free DNase (Boehringer-Mannheim) and used in reverse-transcriptase-PCR reactions. First strand cDNA was primed with oligo-dT using Superscript reverse transcriptase as per manufacturer's direction (Gibco/BRL) and products were amplified with primers hybridizing to the 5' and 3' untranslated regions of CC-CKR-5 (upstream CTCGGATCCGGTGGAACAAGATG-GATTAT (SEQ ID NO: 1); downstream CTCGTCGACAT-GTGCACAACTCTGACTG (SEQ ID NO: 2)) or to glyceraldehyde-3-phosphate dehydrogenase using a Taq/Pwo polymerase mixture (Boehringer Mannheim). To control for the presence of genomic DNA, control cDNA reactions in which reverse transcriptase was omitted were prepared in parallel. These were uniformly negative. To test the linearity of amplification, a ten-fold dilution series (lanes 1–5) starting at 1 pg of pcCKR5 plasmid DNA was amplified under conditions identical to those above. In lane 6, no DNA was added. Monocytes were prepared by overnight adherence to plastic. T cells were prepared from the monocyte-depleted preparation by adherence to anti-CD2-coated beads (Dynal).

Figure 7:
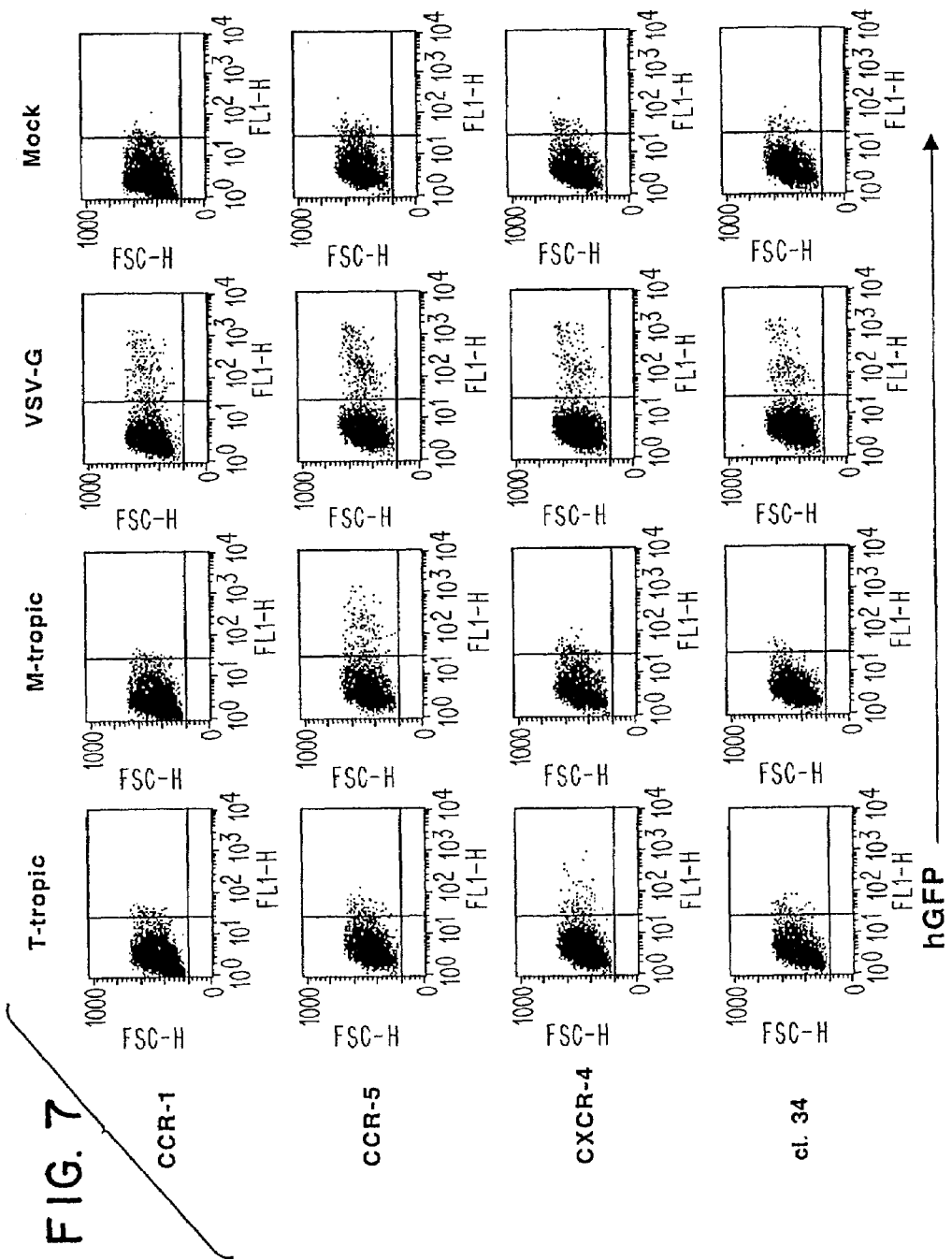

FIG. 7 shows the expression of GFP 48 hours post-infection of GHOST4 cl.34 indicator cells with T-tropic HIV-1 (NL 4-3), M-tropic virus (NL4-3 with BaL Env), or virus pseudotyped with VSV-G. The cells are HOS.CD4 stably transfected with LTR-GFP. Clones 34 (cl. 34) is the parental HOS.CD4 indicator clone transduced with the different chemokine receptors. Forward scatter is indicated on the Y-axis.

DETAILED DESCRIPTION OF THE INVENTION

The term "agent capable of promoting the translocation of macrophage-tropic virus" is used herein interchangeably with the terms "mediator of the entry of envelope glycoproteins of macrophage-trophic strains", "translocating promoter", "translocation promoting agent", "translocating promoting agent" and "translocating promoting protein" refer to a receptor found on membranes of CD4$^+$ cells, that interacts with CD4 in HIV translocation. Specific agents include members of the β-chemokine receptor family. One specific member of the β-chemokine receptor family capable of promoting the translocation of macrophage-tropic virus is CC-CKR-5.

Several lines of evidence implicate chemokine receptors as possible accessory factors in infection by primary strains of HIV-1. First, fusin is a member of the seven transmembrane domain family of chemokine receptors. It is most closely related to the IL-8 receptor, having a homology of 39% in the transmembrane domains. Presumably, fusin is a receptor for some yet unknown chemokine or neuropeptide. Second, the finding that the β-chemokines RANTES, MIP-1α and MIP-1β inhibit infection by primary HIV-1 but not T-tropic virus suggests a role for chemokine receptors in HIV-1 replication and implicates the macrophage-tropic envelope glycoprotein in this process. Third, Paxton et al. [Nat. Med. 2:412–417 (1996)] have shown that the CD4$^+$ cells of individuals that have been multiply exposed to HIV-1 are highly resistant to infection in vitro by primary and macrophage-tropic strains of HIV-1. Resistance to infection was correlated with an overproduction of chemokines. Taken together, these findings suggest a role for chemokines or chemokine receptors in replication of primary but not T-cell line adapted virus. These studies did not address the question of which phase in the viral life cycle was blocked by chemokines.

In one aspect, the present invention relates to the finding that β-chemokines inhibit HIV-1 replication by blocking entry of the virus into CD4$^+$ cells. In light of this finding and those described above, it was surmised that one or more of the β-chemokine receptors serve as a required accessory factor for entry by macrophage-tropic HIV-1. The major members of the CC-CKR family were tested for their ability to facilitate infection with macrophage-tropic HIV-1 strains and fusion with cells expressing envelope glycoproteins from these strains. The results indicate that the product of the recently identified gene encoding C—C Chemokine Receptor 5 (CC-CKR5) acts in concert with CD4 to allow entry of primary macrophage-tropic strains of HIV-1. Thus, CC-CKR5 can be a necessary cofactor for entry of the HIV-1 virus into CD4$^+$ cells.

An initial objective out of which the present invention grew is to understand the mechanism through which HIV gains entrance into target cells. It has been known that the virus binds to CD4, but that CD4 is not sufficient for infection. With the new molecules available, it is possible to study the biochemical events involved in initiation of fusion between the viral envelope and the cellular plasma membrane. The other, and, potentially, more important purpose is to develop a small animal model for HIV, which allows a better understanding of the pathogenesis of AIDS and provides a system for testing potential therapies.

By means of the teachings of the present invention, it is possible to screen for inhibitors of envelope-chemokine receptor interactions, including using analogs of known β chemokines. In conjunction with soluble CD4, this provides a powerful approach for blocking the infectious life cycle prior to viral entry.

The present invention provides animal model systems, developed from the teachings herein, for studying HIV infection and pathogenesis. This allows testing of drugs in an animal system prior to human trials. This discovery allows identification of additional related G-protein coupled receptors that have a role in the broadening of the viral host range in vivo and in pathogenesis in organ systems such as the brain.

This discovery indicates that chemokine receptors encoded by other viruses, particularly members of the Herpes virus family (e.g., CMV, HHV-6, HHV-8), serve to broaden the host range of HIV in individuals infected with both HIV and such viruses. This can therefore increase the range of tissues infected or provide a ligand for HIV envelope that can result in deleterious signal transduction in various tissues. This information could lead to novel approaches to block the synergy between HIV and viral cofactors.

Various additional terms are used in the specification, which are defined as follows:

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

A composition comprising "A" (where "A" is a single protein, DNA molecule, vector, recombinant host cell, etc.) is substantially free of "B" (where "B" comprises one or more contaminating proteins, DNA molecules, vectors, etc.) when at least about 75% by weight of the proteins, DNA, vectors (depending on the category of species to which A and B belong) in the composition is "A". Preferably, "A" comprises at least about 90% by weight of the A+B species in the composition, most preferably at least about 99% by weight. It is also preferred that a composition, which is substantially free of contamination, contain only a single molecular weight species having the activity or characteristic of the species of interest.

The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

In a specific embodiment, the term "about" means within 20%, preferably within 10%, and more preferably within 5%.

Genes Encoding Translocation Promoting Proteins

The present invention contemplates isolation of a gene encoding a translocation promoting of the invention, including a full length, or naturally occurring form of translocation promoting, and any antigenic fragments thereof from any animal, particularly mammalian and more particularly human source. As used herein, the term "gene" refers to an assembly of nucleotides that encode a polypeptide, and includes cDNA and genomic DNA nucleic acids.

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo, i.e., capable of replication under its own control.

A cell has been "transfected" by exogenous or heterologous DNA when such DNA has been introduced inside the cell. A cell has been "transformed" by exogenous or heterologous DNA when the transfected DNA effects a phenotypic change. Preferably, the transforming DNA should be integrated (covalently linked) into chromosomal DNA making up the genome of the cell.

"Heterologous" DNA refers to DNA not naturally located in the cell, or in a chromosomal site of the cell. Preferably, the heterologous DNA includes a gene foreign to the cell.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA—DNA, DNA-RNA and RNA—RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a $T_m$ of 55°, can be used, e.g., 5×SSC, 0.1% SDS, 0.25% milk, and no formamide; or 30% formamide, 5×SSC, 0.5% SDS). Moderate stringency hybridization conditions correspond to a higher $T_m$, e.g., 40% formamide, with 5× or 6×SCC. High stringency hybridization conditions correspond to the highest $T_m$, e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 18 nucleotides; preferably at least about 36 nucleotides; and more preferably the length is at least about 48 nucleotides.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

"Homologous recombination" refers to the insertion of a foreign DNA sequence of a vector in a chromosome. Preferably, the vector targets a specific chromosomal site for homologous recombination. For specific homologous recombination, the vector will contain sufficiently long regions of homology to sequences of the chromosome to allow complementary binding and incorporation of the vector into the chromosome. Longer regions of homology, and greater degrees of sequence similarity, may increase the efficiency of homologous recombination.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the protein encoded by the coding sequence.

A "signal sequence" is included at the beginning of the coding sequence of a protein to be secreted or expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

As used herein, the term "sequence homology" in all its grammatical forms refers to the relationship between proteins that possess a "common evolutionary origin," including proteins from superfamilies (e.g., the immunoglobulin superfamily) and homologous proteins from different species (e.g., myosin light chain, etc.) (Reeck et al., 1987, Cell 50:667).

Accordingly, the term "sequence similarity" in all its grammatical forms refers to the degree of identity or correspondence between nucleic acid or amino acid sequences of proteins that do not share a common evolutionary origin (see Reeck et al., supra). However, in common usage and in the instant application, the term "homologous," when modified with an adverb such as "highly," may refer to sequence similarity and not a common evolutionary origin.

The term "corresponding to" is used herein to refer similar or homologous sequences, whether the exact position is identical or different from the molecule to which the similarity or homology is measured. The term "corresponding to" refers to the sequence similarity, and not the numbering of the amino acid residues or nucleotide bases.

A gene encoding a translocating promoting agent, whether genomic DNA or cDNA, can be isolated from any source, particularly from a human cDNA or genomic library. Methods for obtaining a translocating promoting agent gene are well known in the art, as described above (see, e.g., Sambrook et al., 1989, supra). The DNA may be obtained by standard procedures known in the art from cloned DNA (e.g., a DNA "library"), and preferably is obtained from a cDNA library prepared from tissues with high level expression of the protein (e.g., a macrophage/monocyte or T lymphocyte cDNA library, since these are the cells that evidence highest levels of expression of translocation promoting protein), by chemical synthesis, by cDNA cloning, or by the cloning of genomic DNA, or fragments thereof, purified from the desired cell (See, for example, Sambrook et al., 1989, supra; Glover, D. M. (ed.), 1985, DNA Cloning: A Practical Approach, MRL Press, Ltd., Oxford, U.K. Vol. I, II). Clones derived from genomic DNA may contain regulatory and intron DNA regions in addition to coding regions; clones derived from cDNA will not contain intron sequences. Whatever the source, the gene should be molecularly cloned into a suitable vector for propagation of the gene.

Once the DNA fragments are generated, identification of the specific DNA fragment containing the desired translocating promoting agent gene may be accomplished in a number of ways. For example, if an amount of a portion of a translocating promoting agent gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). For example, a set of oligonucleotides corresponding to the partial amino acid sequence information obtained for the translocating promoting agent protein can be prepared and used as probes for DNA encoding the translocating promoting agent, or as primers for cDNA or mRNA (e. in combination with a poly-T primer for RT-PCR). Preferably, a fragment is selected that is highly unique to the translocating promoting agent of the invention. Those DNA fragments with substantial homology to the probe will hybridize. As noted above, the greater the degree of homology, the more stringent hybridization conditions can be used. In a specific embodiment, stringency hybridization conditions are used to identify a homologous translocating promoting agent gene.

Further selection can be carried out on the basis of the properties of the gene, e.g., if the gene encodes a protein product having the isoelectric, electrophoretic, amino acid composition, or partial amino acid sequence of translocating promoting agent as disclosed herein. Thus, the presence of the gene may be detected by assays based on the physical, chemical, immunological, or functional properties of its expressed product. For example, cDNA clones, or DNA clones which hybrid-select the proper mRNAs, can be selected which produce a protein that, e.g., has similar or identical electrophoretic migration, isoelectric focusing or non-equilibrium pH gel electrophoresis is behavior, proteolytic digestion maps, or antigenic properties as known for the translocating promoting agent. For example, the polyclonal antibody to the murine translocating promoting agent, described in infra, can be used to confirm expression of the translocating promoting agent, (either murine and human).

The present invention also relates to genes encoding analogs and derivatives of the translocating promoting agent of the invention, that have the same or homologous functional activity as the translocating promoting agent, and homologs thereof from other species. The production and use of derivatives and analogs related to the translocating promoting agent are within the scope of the present invention. In a specific embodiment, the derivative or analog is functionally active, i.e., capable of exhibiting one or more functional activities associated with a full-length, wild-type translocating promoting agent of the invention. In another embodiment, the translocating promoting agent contains a different cytoplasmic domain, e.g., which associates the protein with the cell membrane but does not mediate G protein activation, translocation, or both.

Derivatives of translocation promoting agents can be made by altering nucleic acids encoding translocation promoting agents by substitutions, additions or deletions that provide for functionally modified molecules. Preferably, derivatives are made that have diminished HIV-translocational activity relative to the native translocating promoting agent. Other derivatives may encode soluble fragments of the translocating promoting agent extracellular domain that have the lower affinity for the natural ligand of the translocating promoting agent of the invention but greater affinity for an HIV envelope protein. Such soluble derivatives may be potent inhibitors of HIV binding to the translocation promoting agent on cells, e.g., to CC-CKR5 on macrophages and T cells.

Due to the degeneracy of nucleotide coding sequences, other DNA sequences which encode substantially the same amino acid sequence as a translocating promoting agent gene may be used in the practice of the present invention. These include but are not limited to allelic genes, homologous genes from other species, and nucleotide sequences comprising all or portions of translocating promoting agent genes which are altered by the substitution of different codons that encode the same amino acid residue within the sequence, thus producing a silent change. Likewise, the translocating promoting agent derivatives of the invention include, but are not limited to, those containing, as a primary amino acid sequence, all or part of the amino acid sequence of a translocating promoting agent protein including altered sequences in which functionally equivalent amino acid residues are substituted for residues within the sequence resulting in a conservative amino acid substitution. For example, one or more amino acid residues within the sequence can be substituted by another amino acid of a similar polarity, which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. Amino acids containing aromatic ring structures are phenylalanine, tryptophan, and tyrosine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Such alterations will not be expected to affect apparent molecular weight as determined by polyacrylamide gel electrophoresis, or isoelectric point.

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

The genes encoding translocating promoting agent derivatives and analogs of the invention can be produced by various methods known in the art. The manipulations which result in their production can occur at the gene or protein level. For example, the cloned translocating promoting agent gene sequence can be modified by any of numerous strategies known in the art (Sambrook et al., 1989, supra). The sequence can be cleaved at appropriate sites with restriction endonuclease(s), followed by further enzymatic modification if desired, isolated, and ligated in vitro. In the production of the gene encoding a derivative or analog of translocating promoting agent, care should be taken to ensure that the modified gene remains within the same translational reading frame as the translocating promoting agent gene, uninterrupted by translational stop signals, in the gene region where the desired activity is encoded.

Additionally, the translocation promoting agent-encoding nucleic acid sequence can be mutated in vitro or in vivo, to create and/or destroy translation, initiation, and/or termination sequences, or to create variations in coding regions and/or form new restriction endonuclease sites or destroy preexisting ones, to facilitate further in vitro modification. Preferably, such mutations diminish the HIV translocation activity of the mutated translocating promoting agent gene product. Any technique for mutagenesis known in the art can be used, including but not limited to, in vitro site-directed mutagenesis (Hutchinson, C., et al., 1978, J. Biol. Chem. 253:6551; Zoller and Smith, 1984, DNA 3:479–488; Oliphant et al., 1986, Gene 44:177; Hutchinson et al., 1986, Proc. Natl. Acad. Sci. U.S.A. 83:710), use of TAB® linkers (Pharmacia), etc. PCR techniques are preferred for site directed mutagenesis (see Higuchi, 1989, "Using PCR to Engineer DNA", in *PCR Technology: Principles and Applications for DNA Amplification*, H. Erlich, ed., Stockton Press, Chapter 6, pp. 61–70).

The identified and isolated gene can then be inserted into an appropriate cloning vector. A large number of vector-host systems known in the art may be used. Possible vectors include, but are not limited to, plasmids or modified viruses, but the vector system must be compatible with the host cell used. Examples of vectors include, but are not limited to, *E. coli*, bacteriophages such as lambda derivatives, or plasmids such as pBR322 derivatives or pUC plasmid derivatives, e.g., pGEX vectors, pmal-c, pFLAG, etc. The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Recombinant molecules can be introduced into host cells via transformation, transfection, infection, electroporation, etc., so that many copies of the gene sequence are generated. Preferably, the cloned, gene is contained on a shuttle vector plasmid, which provides for expansion in a cloning cell, e.g., *E. coli*, and facile purification for subsequent insertion into an appropriate expression cell line, if such is desired. For example, a shuttle vector, which is a vector that can replicate in more than one type of organism, can be prepared for replication in both *E. coli* and *Saccharomyces cerevisiae* by linking sequences from an *E. coli* plasmid with sequences form the yeast 2μ plasmid.

In an alternative method, the desired gene may be identified and isolated after insertion into a suitable cloning vector in a "shot gun" approach. Enrichment for the desired gene, for example, by size fractionation, can be done before insertion into the cloning vector.

Expression of Translocation Promoting Agents

The nucleotide sequence coding for translocation promoting agent, or antigenic fragment, derivative or analog thereof, including a chimeric protein, thereof, can be inserted into an appropriate expression vector, i.e., a vector which contains the necessary elements for the transcription and translation of the inserted protein-coding sequence. Such elements are termed herein a "promoter." Thus, the nucleic acid encoding translocation promoting of the invention is operationally associated with a promoter in an expression vector of the invention. Both cDNA and genomic sequences can be cloned and expressed under control of such regulatory sequences. An expression vector also preferably includes a replication origin.

The necessary transcriptional and translational signals can be provided on a recombinant expression vector, or they may be supplied by the native gene encoding translocation promoting and/or its flanking regions.

As pointed out above, potential chimeric partners for translocation promoting include other transmembrane domains, or a domain for modification with a phospholipid anchor.

Potential host-vector systems include but are not limited to mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

A recombinant translocation promoting agent of the invention, or fragment, derivative, chimeric construct, or analog thereof, may be expressed chromosomally, after integration of the coding sequence by recombination. In this regard, any of a number of amplification systems may be used to achieve high levels of stable gene expression (See Sambrook et al., 1989, supra).

The cell into which the recombinant vector comprising the nucleic acid encoding translocation promoting agent is cultured in an appropriate cell culture medium under conditions that provide for expression of translocation promoting agent by the cell.

Any of the methods previously described for the insertion of DNA fragments into a cloning vector may be used to construct expression vectors containing a gene consisting of appropriate transcriptional/translational control signals and the protein coding sequences. These methods may include in vitro recombinant DNA and synthetic techniques and in vivo recombination (genetic recombination).

Expression of translocation promoting an agent may be controlled by any promoter/enhancer element known in the art, but these regulatory elements must be functional in the host selected for expression. In one embodiment the translocation promoting agent is under the control of the CD4 enhancer/promoter/silencer, as described [Killeen et al., (1993) supra]. Promoters which may be used to control translocation promoting gene expression include, but are not limited to, the SV40 early promoter region (Benoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the P-lactamase promoter (Villa-Kamaroff, et al., 1978, Proc. Natl. Acad. Sci. U.S.A. 75:3727–3731), or the tac promoter (DeBoer, et al., 1983. Proc. Natl. Acad. Sci. U.S.A.

80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter; and the animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58), alpha 1-antitrypsin gene control region which is active in the liver (Kelsey et al., 1987, Genes and Devel. 1: 161–171), beta-globin gene control region which is active in myeloid cells (Mogram et al., 1985. Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col E1, pCR1, pBR322, pMal-C2, pET, pGEX (Smith et al., 1988, Gene 67:31–40), pMB9 and their derivatives. plasmids such as RP4; phage DNAS, e.g., the numerous derivatives of phage λ, e.g., NN1989, and other phage DNA, e.g., M13 and filamentous single stranded phage DNA: yeast plasmids such as the 2μ plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

In addition, a host cell strain may be chosen which modulates the expression of the inserted sequences, or modifies and processes the gene product in the specific fashion desired. Different host cells have characteristic and specific mechanisms for the translational and post-translational processing and modification (e.g., glycosylation, cleavage [e.g., of signal sequence]) of proteins. Appropriate cell lines or host systems can be chosen to ensure the desired modification and processing of the foreign protein expressed. For example, expression in a bacterial system can be used to produce an nonglycosylated core protein product. However, the transmembrane translocation promoting agent expressed in bacteria may not be properly folded. Expression in yeast can produce a glycosylated product. Expression in eukaryotic cells can increase the likelihood of "native" glycosylation and folding of a heterologous protein. Moreover, expression in mammalian cells can provide a tool for reconstituting, or constituting, translocation promoting activity. Furthermore, different vector/host expression systems may affect processing reactions, such as proteolytic cleavages, to a different extent.

Vectors are introduced into the desired host cells by methods known in the art. e.g., transfection, electroporation, microinjection, transduction, cell fusion, DEAE dextran, calcium phosphate precipitation, lipofection (lysosome fusion), use of a gene gun, or a DNA vector transporter (see, e.g., Wu et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

A recombinant translocation promoting agent expressed as an integral membrane protein can be isolated and purified by standard methods. Generally, the integral membrane protein can be obtained by lysing the membrane with detergents. such as but not limited to, sodium dodecyl sulfate (SDS), Triton X-100, nonidet P-40 (NP-40), digoxin, sodium deoxycholate, and the like, including mixtures thereof. Solubilization can be enhanced by sonication of the suspension. Soluble forms of the protein can be obtained by collecting culture fluid, or solubilizing inclusion bodies, e.g., by treatment with detergent, and if desired sonication or other mechanical processes, as described above. The solubilized or soluble protein can be isolated using various techniques, such as polyacrylamide gel electrophoresis (PAGE), isoelectric focusing, 2-dimensional gel electrophoresis, chromatography (e.g., ion exchange, affinity, immunoaffinity, and sizing column chromatography), centrifugation, differential solubility, immunoprecipitation, or by any other standard technique for the purification of proteins.

For the assays of the invention that depend on evaluating the activity of the translocation promoting protein, preferably the gene encoding the protein is transfected or used to transform host cells. More preferably, such host cells are transfected to co-express human CD4, and more preferably, such cells lack the ability to express an endogenous or native translocation promoting agent. Co-expression of the translocation promoting agent and CD4 facilitates HIV translocation, which is the endpoint for an assay to identify antagonists of HIV translocation.

Antibodies to Translocation Promoting Protein

According to the invention, the translocation promoting agent produced recombinantly or by chemical synthesis, and fragments or other derivatives or analogs thereof, including fusion proteins, may be used as an immunogen to generate antibodies that recognize the translocation promoting protein. Such antibodies include but are not limited to polyclonal, monoclonal, chimeric, single chain, Fab fragments, and an Fab expression library. The anti-translocation promoting agent antibodies of the invention may be cross reactive, e.g., they may recognize translocation promoting agent from different species. Polyclonal antibodies have greater likelihood of cross reactivity. Alternatively, an antibody of the invention may be specific for a single form of translocation promoting agent, such as the murine translocation promoting agent. Preferably, such an antibody is specific for human translocation promoting agent.

In a specific embodiment, an antibody of the invention is specific for a masked epitope on the translocation promoting agent that is exposed on binding to HIV. In another embodiment, an antibody of the invention is specific for an epitope created by the binding of the translocation promoting agent with HIV or CD4, or both. For example, the binding of HIV envelope protein to CD4 induces a conformational change in gp120 or gp130, which results in an increased affinity of GP120 or gp130 for CC-DKR5, and possibly a concomitant unmasking of a CC-CKR5 epitope. Such antibodies can be selected on the basis of binding under conditions of HIV binding to the translocation promoting agent, e.g., at 4° C. to inhibit translocation, and screened for non-binding to the free translocation promoting agent.

Various procedures known in the art may be used for the production of polyclonal antibodies to the translocation promoting agent or derivative or analog thereof. For the production of antibody, various host animals can be immunized by injection with the translocation promoting agent, or a derivative (e.g., fragment or fusion protein) thereof, including but not limited to rabbits, mice, rats, sheep, goats, etc. In one embodiment, the translocation promoting agent or fragment thereof can be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum.*

For preparation of monoclonal antibodies directed toward the translocation promoting agent, or fragment, analog, or derivative thereof, any technique that provides for the production of antibody molecules by continuous cell lines in culture may be used. These include but are not limited to the hybridoma technique originally developed by Kohler and Milstein [*Nature* 256:495–497 (1975)], as well as the trioma technique, the human B-cell hybridoma technique [Kozbor et al., *Immunology Today* 4:72 1983); Cote et al., *Proc. Natl. Acad. Sci. U.S.A.* 80:2026–2030 (1983)], and the EBV-hybridoma technique to produce human monoclonal antibodies [Cole et al., in *Monoclonal Antibodies and Cancer Therapy*, Alan R. Liss, Inc., pp. 77–96 (1985)]. In an additional embodiment of the invention, monoclonal antibodies can be produced in germ-free animals utilizing recent technology [PCT/US90/02545]. In fact, according to the invention, techniques developed for the production of "chimeric antibodies" [Morrison et al., *J. Bacteriol.* 159:870 (1984); Neuberger et al., *Nature* 312:604–608 (1984); Takeda et al., *Nature* 314:452–454 (1985)] by splicing the genes from a mouse antibody molecule specific for an translocation promoting protein together with genes from a human antibody molecule of appropriate biological activity can be used; such antibodies are within the scope of this invention. Such human or humanized chimeric antibodies are preferred for use in therapy of human diseases or disorders (described infra), since the human or humanized antibodies are much less likely than xenogenic antibodies to induce an immune response, in particular an allergic response, themselves.

According to the invention, techniques described for the production of single chain antibodies [U.S. Pat. Nos. 5,476,786 and 5,132,405 to Huston; U.S. Pat. No. 4,946,778] can be adapted to produce translocation promoting protein-specific single chain antibodies. An additional embodiment of the invention utilizes the techniques described for the construction of Fab expression libraries [Huse et al., *Science* 246:1275–1281 (1989)] to allow rapid and easy identification of monoclonal Fab fragments with the desired specificity for an translocation promoting protein, or its derivatives, or analogs.

Antibody fragments which contain the idiotype of the antibody molecule can be generated by known techniques. For example, such fragments include but are not limited to: the $F(ab')_2$ fragment which can be produced by pepsin digestion of the antibody molecule; the Fab' fragments which can be generated by reducing the disulfide bridges of the $F(ab')_2$ fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of an translocation promoting protein, one may assay generated hybridomas for a product which binds to an translocation promoting protein fragment containing such epitope. For selection of an antibody specific to an translocation promoting protein from a particular species of animal, one can select on the basis of positive binding with translocation promoting agent expressed by or isolated from cells of that species of animal.

The foregoing antibodies can be used in methods known in the art relating to the localization and activity of the translocation promoting agent, e.g., for Western blotting, imaging translocation promoting agent in situ, measuring levels thereof in appropriate physiological samples, etc. using any of the detection techniques mentioned above or known in the art.

Suitable labels for antibodies include enzymes, fluorophores (e.g., fluorescene isothiocyanate (FITC), phycoerythrin (PE), Texas red (TR), rhodamine, free or chelated lanthanide series salts, especially $Eu^3$+green fluorescent protein, to name a few fluorophores), chromophores, radioisotopes, chelating agents, dyes, colloidal gold, latex particles, ligands (e.g., biotin), and chemiluminescent agents. When a control marker is employed, the same or different labels may be used for the receptor and control marker. In the instance where a radioactive label, such as the isotopes $^3H$, $^{14}C$, $^{32}p$, $^{35}s$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is a protein, e.g., an enzyme or fluorescent protein, detection may be accomplished by any of the presently utilized colorimetric, spectrophotometric, fluorospectrophotometric, amperometric or gasometric techniques known in the art.

Direct labels are one example of labels which can be used according to the present invention. A direct label has been defined as an entity, which in its natural state, is readily visible, either to the naked eye, or with the aid of an optical filter and/or applied stimulation, e.g., U.V. light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionucleotide, a fluorescent moiety or a luminescent moiety. In addition to these direct labelling devices, indirect labels comprising enzymes can also be used according to the present invention.

Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Eva Engvall in Enzyme Immunoassay ELISA and EMIT in *Methods in Enzymology,* 70. 419–439, 1980 and in U.S. Pat. No. 4,857, 453. Suitable enzymes include, but are not limited to. alkaline phosphatase and horseradish peroxidase.

Other labels for use in the invention include magnetic beads or magnetic resonance imaging labels.

In another embodiment, a phorphorylation site can be created on an antibody of the invention for labeling with $^{32}P$, e.g., as described in European Patent No. 0372707 (application No. 89311108.8) by Sidney Pestka, or U.S. Pat. No. 5,459,240, issued Oct. 17, 1995 to Foxwell et al.

As exemplified herein, proteins, including antibodies, can be labeled by metabolic labeling. Metabolic labeling occurs during in vitro incubation of the cells that express the protein in the presence of culture medium supplemented with a metabolic label, such as $[^{35}S]$-methionine or $[^{32}P]$-orthophosphate. In addition to metabolic (or biosynthetic) labeling with $[^{35}S]$-methionine, the invention further contemplates labeling with $[^{14}C]$-amino acids and $[^{3}H]$-amino acids (with the tritium substituted at non-labile positions).

In a specific embodiment, antibodies that agonize or antagonize the activity of translocation promoting protein can be generated. Such antibodies can be tested using the assays described infra for identifying ligands.

Such antibodies, when conjugated with a toxin or radioactive element, can be used to target HIV-permissive cells for destruction. Thus, cells harboring HIV, particularly in its dormant phase, can be destroyed with antibodies, e.g., conjugated to a toxin such as ricin or a radioisotope such as $^{32}P$ or $^{125}I$, when such antibodies are specific for the translocation promoting protein.

Methods for Screening Drug Libraries for Compounds Useful in the Treatment and/or Prevention of HIV Infection.

Cell lines expressing CD4 and one or more members of the chemokine receptor family are infected with an HIV-reporter virus that is pseudotyped with one or more selected envelope glycoproteins. Compound libraries are assayed for their ability to inhibit infection of the cells by the pseudotyped virus. Candidate compounds are selected and then counter-screened for non-specific effects on infection with virus pseudotyped with non-HIV envelope proteins such as MLV amphotropic env or with VSV-G env.

Cell lines include, but are not limited to murine 3T3 cells, human HeLa, U87MG, HOS, and 293 cells. In a specific embodiment, HOS.CD4 cells are used that are transfected with a construct containing Green Fluorescent Protein under the regulation of HIV-2 LTR. Additional human cell lines that do not normally express either fusin or CKR-5 (such as SCL) can also be used.

HIV vectors include, but are not limited to HIV-luciferase, HIV-alkaline phosphatase, HIV-CD24 and HIV-2 LTR-Green Fluorescent Protein. In these vectors, the env gene is inactivated by frame shifting, and the reporter gene is inserted to replace the Nef open reading frame. Additional vectors can be made for easier screening in murine cells, in which expression of HIV-LTR-driven reporters is only about 1% of the level in human cells. Such vectors are based on the HIV-gpt prototype (Page et al. 1990), such that the reporter, e.g. luciferase is placed under control of the SV40 promoter within the env gene, ensuring high level expression following integration.

Envelope glycoproteins that are appropriate for screening CKR-5-transfected cells include, but are not be limited to, envs of JR-FL, ADA, and BaL primary isolates. Envelope glycoproteins that are appropriate for screening cells expressing fusin include HXB2, 5F2, and NL4-3 as well as HIV-2ROD. Envelope glycoproteins of SIVmac can also be used to assay inhibition of CKR-5 co-receptor function.

The following is a list of documents related to the above disclosure and particularly to the experimental procedures and discussions. These documents, and all others cited above, should be considered as incorporated by reference in their entirety.

Identification of Antagonists of HIV Translocation

Identification and isolation of a gene encoding a translocation promoting agent of the invention provides for expression of translocation promoting agent in quantities greater than can be isolated from natural sources, or in indicator cells that are specially engineered to indicate the activity of translocation promoting protein expressed after transfection or transformation of the cells. Accordingly, the present invention contemplates an alternative method for identifying agonists and antagonists of HIV translocation directed to modulating the activity of the translocation promoting agent using various screening assays known in the art. In one embodiment, such agonists or antagonists competitively inhibit HIV binding, or more particularly, an HIV envelope protein binding to the translocation promoting agent; in another embodiment, the agonist or antagonist indirectly affects HIV translocation. whether by non-competitive binding to the translocation promoting agent, or by affecting the level of expression of the translocation promoting agent.

Any screening technique known in the art can be used to screen for antagonists of CD4-HIV envelope-translocation promoting agent association. The present invention contemplates screens for small molecule ligands or ligand analogs and mimics, as well as screens for natural ligands that bind to and antagonize such activity in vivo. For example, natural products libraries can be screened using assays of the invention for molecules that antagonize HIV-translocation promoting activity.

Identification and screening of antagonists is further facilitated by determining structural features of the protein. e.g., using X-ray crystallography, neutron diffraction. nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, 1990, *Science* 249:386–390 (1990); Cwirla, et al., *Proc. Natl. Acad. Sci.,* 87:6378–6382 (1990); Devlin et al., *Science,* 249:404–406 (1990)], very large libraries can be constructed ($10^6$–$10^8$ chemical entities). A second approach uses primarily chemical methods, of which the Geysen method [Geysen et al., *Molecular Immunology* 23:709–715 (1986); Geysen et al. *J. Immunologic Method* 102:259–274 (1987)] and the method of Fodor et al. [Science 251:767–773 (1991)] are examples. Furka et al. [14*th International Congress of Biochemistry,* Volume 5, Abstract FR:013 (1988); Furka, *Int. J. Peptide Protein Res.* 37:487493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA* 90:10700–4 (1993); Ohlmeyer et al., *Proc. Natl. Acad. Sci. USA* 90:10922–10926 (1993); Lam et al., International Patent Publication No. WO 92/00252; Kocis et al., International Patent Publication No. WO 9428028, each of which is incorporated herein by reference in its entirety], and the like can be used to screen for translocation promoting protein ligands according to the present invention.

Alternatively, assays for binding of natural ligand to cells that express recombinant forms of a translocation promoting protein ligand binding domain, for fusin for example, can be performed. The soluble ligands can be provided readily as recombinant or synthetic proteins.

The screening can be performed with recombinant cells that express the translocation promoting agent, or alternatively, using purified protein, e.g., produced recombinantly, as described above. For example, the ability of a labeled, soluble or solubilized translocation promoting agent that includes the ligand-binding portion of the molecule, to bind ligand can be used to screen libraries, as described in the foregoing references.

Administration of Antagonists of the CC-CKR-5 (CD4-gp120-gp41) Complex

According to the invention, the component or components of a therapeutic composition of the invention may be introduced parenterally, transmucosally, e.g., orally, nasally, or rectally, or transdermally. Preferably, administration is parenteral, e.g., via intravenous injection, and also including, but is not limited to, intra-arteriole, intramuscular, intradermal, subcutaneous, intraperitoneal, intraventricular, and intracranial administration. More preferably, where administration of an antagonist to the CC-CKR-5-(CD4-pg120-gp41) complex is administered to prevent or treat AIDs, it may be introduced by injection into the blood. The antagonist may be a specific antibody raised against the CC-CKR-5-(CD4-gp120-gp41)complex or a CC-CKR-5 mimic that competitively competes with CC-CKR-5 for the (CD4-gp120-gp41)complex.

In another embodiment, the therapeutic compound can be delivered in a vesicle, in particular a liposome [see Langer, *Science* 249:1527–1533 (1990); Treat et al., in *Liposomes in the Therapy of Infectious Disease and Cancer,* Lopez-Berestein and Fidler (eds.), Liss: New York, pp. 353–365 (1989); Lopez-Berestein, ibid., pp. 317–327; see generally ibid.]. To reduce its systemic side effects, this may be a preferred method for introducing an antagonist to CC-CKR-5.

In yet another embodiment, the therapeutic compound can be delivered in a controlled release system. For example, an antibody may be administered using intravenous infusion, an implantable osmotic pump, a transdermal patch, liposomes, or other modes of administration. In one embodiment, a pump may be used [see Langer, supra; Sefton, *CRC Crit. Ref Biomed. Eng.* 14:201 (1987); Buchwald et al., *Surgery* 88:507 (1980); Saudek et al., *N. Engl. J. Med.* 321:574 (1989)]. In another embodiment, polymeric materials can be used [see *Medical Applications of Controlled Release,* Langer and Wise (eds.), CRC Press: Boca Raton, Fla. (1974); *Controlled Drug Bioavailability, Drug Product Design and Performance,* Smolen and Ball (eds.), Wiley: New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)]. In yet another embodiment, a controlled release system can be placed in proximity of a therapeutic target, e.g., the brain, thus requiring only a fraction of the systemic dose [see, e.g., Goodson, in *Medical Applications of Controlled Release,* supra, vol. 2, pp. 115–138 (1984)].

Other controlled release systems are discussed in the review by Langer [*Science* 249:1527–1533 (1990)].

Thus, the antagonist can be delivered by intravenous, intraarterial, intraperitoneal, intramuscular, or subcutaneous routes of administration. Alternatively, the antagonist, properly formulated, can be administered by nasal or oral administration. A constant supply of the antagonist can be ensured by providing a therapeutically effective dose (i.e., a dose effective to induce metabolic changes in a subject) at the necessary intervals, e.g., daily, every 12 hours, etc. These parameters will depend on the severity of the disease condition being treated, other actions, such as diet modification, that are implemented, the weight, age, and sex of the subject, and other criteria, which can be readily determined according to standard good medical practice by those of skill in the art.

A subject in whom administration of the antagonist is an effective-therapeutic regiment for AIDS is preferably a human, but can be a primate with a related viral condition. Thus, as can be readily appreciated by one of ordinary skill in the art, the methods and pharmaceutical compositions of the present invention are particularly suited to administration to any primate.

Transigenic Vectors and Inhibition of Expression

In one embodiment, a gene encoding a translocation promoting agent, or antisense or ribozyme specific for translocation promoting agent mRNA (termed herein an "antigene") is introduced in vivo in a viral vector. Such vectors include an attenuated or defective DNA virus, such as but not limited to herpes simplex virus (HSV), papillomavirus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus macrophage can be specifically targeted. Examples of particular vectors include, but are not limited to, a defective herpes virus 1 (HSV1) vector [Kaplitt et al., *Molec. Cell. Neurosci.* 2:320–330 (1991)], an attenuated adenovirus vector, such as the vector described by Stratford-Perricaudet et al. [*J. Clin. Invest.* 90:626–630 (1992)], and a defective adeno-associated virus vector [Samulski et al., *J. Virol.* 61:3096–3101 (1987); Samulski et al., *J. Virol.* 63:3822–3828 (1989)].

In another embodiment the gene or antigene can be introduced in a retroviral vector, e.g., as described in Anderson et al., U.S. Pat. No. 5,399,346; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; International Patent Publication No. WO 95/07358, published Mar. 16, 1995, by Dougherty et al.; and Kuo et al., 1993, Blood 82:845.

In one embodiment. specific PBMCs are removed from an HIV-positive subject animal (e.g., a human) and the gene encoding CC-CKR5 is replaced by a modified CC-CKR5 that retains its β-chemokine binding activity but cannot translocate HIV. The subject animal is depleted of its corresponding PBMCs (e.g., if the gene modification was performed in a macrophage or T-cell, then the macrophages or T-cell are depleted) and the modified PBMCs are reintroduced into the subject animal. Such an animal subject should then have macrophage, for example, which are capable of responding to the appropriate chemokines, but which are no longer susceptible to HIV translocation/infection.

Targeted gene delivery is described in International Patent Publication WO 95/28494, published October 1995.

Alternatively, the vector can be introduced in vivo by lipofection [Felgner, et. al., *Proc. Natl. Acad. Sci. U.S.A.* 84:7413–7417 (1987); see Mackey, et al., *Proc. Natl. Acad. Sci. U.S.A.* 85:8027–8031 (1988); Felgner and Ringold, *Science* 337:387–388 (1989)]. Lipids may be chemically coupled to other molecules for the purpose of targeting [see Mackey, et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al., *J. Biol. Chem.* 267:963–967 (1992); Wu and Wu, *J. Biol. Chem.* 263: 14621–14624 (1988); Hartmut et al., Canadian Patent Application No. 2,012,311, filed Mar. 15, 1990].

As noted above, the present invention extends to the preparation of antisense nucleotides and ribozymes that may be used to interfere with the expression of translocation promoting agent at the translational level. This approach utilizes antisense nucleic acid and ribozymes to block translation of a specific mRNA, either by masking that mRNA with an antisense nucleic acid or cleaving it with a ribozyme. Such antisense or ribozyme nucleic acids may be produced chemically, or may be expressed from an "antigen."

Antisense nucleic acids are DNA or RNA molecules that are complementary to at least a portion of a specific mRNA molecule [see Marcus-Sekura, *Anal. Biochem.* 172:298 (1988)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into organ cells. Antisense methods have been used to inhibit the expression of many genes in vitro [Marcus-Sekura, 1988, supra; Hambor et al., *J. Exp. Med.* 168:1237 (1988)]. Preferably synthetic antisense nucleotides contain phosphoester analogs, such as phosphorothiolates, or thioesters, rather than natural phosphoester bonds. Such phosphoester bond analogs are more resistant to degradation, increasing the stability, and therefore the efficacy, of the antisense nucleic acids.

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, *J. Am. Med. Assoc.* 260:3030 (1988)]. Because they are sequence-specific, only mRNAs with particular sequences are inactivated.

Investigators have identified two types of ribozymes, *Tetrahymena*-type and "hammerhead"-type. *Tetrahymena*-type ribozymes recognize four-base sequences, while "hammerhead"-type recognize eleven- to eighteen-base sequences. The longer the recognition sequence, the more likely it is to occur exclusively in the target MRNA species. Therefore, hammerhead-type ribozymes are preferable to *Tetrahymena*-type ribozymes for inactivating a specific mRNA species, and eighteen base recognition sequences are preferable to shorter recognition sequences.

The DNA sequences encoding the translocation promoting agent can be used to prepare antisense molecules against and ribozymes that cleave mRNAs for translocation promoting agent, thus inhibiting expression of the gene encoding the translocation promoting agent, which can reduce the level of HIV translocation in macrophages and T cells.

Transgenic Mice

The transgenic mice of the present application are produced as detailed in Killeen et al. (1993) EMBO 12 1547–1553, which is hereby incorporated by reference. The construction of the human $CD4^+$ murine $CD4^-$ mice are described by Killeen et al. (1993) EMBO 12 1547–1553. A CC-CKR-5 transgene is constructed using a human CC-CKR-5 minigene that includes all of the coding region exons and ~3 kb of sequence (including the first intron) upstream of the coding sequence. B6/SIL F2 eggs or B6/SIL F1× human $CD4^+$/murine $CD4^-$ eggs are microinjected with the human CC-CKR-5 transgene according to standard procedures described by Hogan et al. (1986). Founders are identified by Southern blotting using a human CC-CKR-5 cDNA probe.

Cells on Solid Support

Solid supports include glass beads, sugar beads (SEPHADEX, SEPHAROSE, Agarose, SEPHACEL etc.) magnetic beads, and dowex-type materials. Biological materials may be passed through cells bound to solid supports by common methods know to any person skilled in the art including but not limited by batchwise, by centrifugation, pressure-membrane filtration (e.g. Amicon or Millipore filtration) and through various types of columns.

EXAMPLE 1

CC-CKR-5 and CD4 Function Cooperatively to Mediate Entry of Macrophage-Tropic Virus

Methods

NL4-3-Luc-$R^-E^-$ virus stocks pseudotyped by various Envs were generated by transfecting 293T cells with 10 μg each of pNL4-3-Luc-R⁻E⁻ and pcDNAI-based expression vectors (InVitrogen) encoding JRFL, ADA, BaL, HXB2 or amphotropic MLV Env. Virus-containing supernatants were harvested 48 hours post-transfection and frozen in aliquots at −80°. Viruses were quantitated by ELISA assay for p24. Cells ($5 \times 10^4$) were seeded in 48-well dishes in DMEM containing 10% fetal bovine serum and infected with luciferase reporter virus (50 ng p24) in a total volume of 400 µl with or without 30 minutes pretreatment with each of the chemokines listed (500 ng/ml, Peprotech). After 16 hours, 0.5 ml medium was added to the wells. After 4 days of additional culture, 100 µl lysates were prepared and luciferase activity in 20 µl was assayed using commercially available reagents (Promega) (see FIG. 1).

Cell lines stably expressing chemokine receptors or fusin-GFP were established as previously described. Briefly, cDNAs encoding the indicated receptors were subcloned into pBABE-puro and transfected into BING packaging cells. 48 hour later supernatants were collected and used to infect NIH3T3 (3T3), 3T3.CD4, HOS, HOS.CD4, Hela, and Hela.CD4. Amphotropic virus stocks were prepared by transfecting BING packaging cells [Pear et al., *Proc. Nat. Acad. Sci USA* 90:8392–8396 (1993)] with the resulting plasmics or by a previous method [Pear et al. (1993) supra; Geo et al., *J. Biol. Chem.* 269: 28539–28542 (1994)] with the substitution of 293T cells for COS cells. After 48 hours cells were selected for puromycin resistance. One week after start of selection, puro-resistant populations were collected and tested for infectability by pseudotyped luciferase reporter virus (100 ng p24 per infection). For antibody blocking experiments, cells were preincubated with anti-CD4 mAb (Leu3a, Becton Dickinson) at 10 µg/ml for 1 hour before infection with virus. Anti-CD4 was maintained during infection at 5 ug/ml. For chemokine blocking experiments. cells were preincubated with a mixture of MIP-1α, MIP-1β, and RANTES (each at 1 µg/ml). After 30 minutes, an equal volume of reporter virus was added without additional chemokines, and luciferase activity was measured 2 days later. For the calcium mobilization assays. cells were loaded with the calcium indicator indo-1/AM at 2 mM in complete growth medium at 20° C. for 45 minutes. Cells were then washed, resuspended in Na—HBSS (in mM: 2 $CaCl_2$, 145 NaCl, 5 KCl, 1 $MgCl_2$, 5 d-glucose, 20 HEPES; pH 7.3) containing 1% BSA and maintained at 20° C. for up to two hours. Fluorescence measurements to determine $[Ca^{2+}]_i$ were made from approximately $5 \times 10^5$ cells suspended in 2 ml Na—HBSS and maintained at 37° C. in a constantly stirred acrylic cuvette using a Photon Technologies Inc. spectrofluorimeter. The excitation wavelength was 350 nm (4 nm bandwidth) and dual simultaneous monitoring of emission at 405 and 485 nm (10 nm bandwidth) was employed. The ratio of emission at 405/485 nm was measured at a rate of 2 Hz (See FIG. 3).

Results

Chemokines Block Entry of Primary HIV-1

To test whether β-chemokines block entry of macrophage-tropic HIV-1, the T cell line PM1 is infected with HIV-1-based luciferase reporter viruses. PM1 cells are highly susceptible to infection with both macrophage-tropic and T-tropic virus. The luciferase reporter viruses infect cells in a single round but are not competent for further replication because of a frameshift mutation inserted in env. Thus, measurement of luciferase activity in cells infected with pseudotypes of this virus permit comparison of the relative efficiency of entry mediated by different Envs. In these studies, HXB2 is used as a representative T-tropic Env, whereas JRFL, ADA, and BaL, are used as macrophage-tropic Envs. In addition, to control for possible post-entry or nonspecific effects of β-chemokines, virus pseudotyped with amphotropic murine leukemia virus (A-MLV) Env is prepared.

The β-chemokines inhibited infection of PM1 cells with virus pseudotyped by macrophage-tropic Env (JRFL, ADA, BaL). However, the chemokines have no effect on infection with virus bearing T-tropic (HXB2) or A-MLV envelopes (FIG. 1A-1B). Strongest blocking is observed with RANTES, while MIP-1β and MIP-1α followed in order of effectiveness. MCP-3 and eotaxin have no inhibitory effect (FIG. 1A-1B). This same order is observed in inhibition of primary HIV-1 replication by β-chemokines. Taken together, these findings indicate that βchemokine inhibition of viral replication is due to prevention of entry of macrophage-tropic HIV-1, but not T-tropic HIV-1.

CC-CKR-5 is a Potent Co-Receptor for Macrophage-tropic Virus

The known β-chemokine receptors, including fusin, are expressed in several human and murine cell lines and then their relative infectivity is tested using HIV-luciferase pseudotyped with the different envelope glycoproteins. Human embryonic kidney 293T cells transiently transfected with both CD4 and the different chemokine receptors are readily infected with virus pseudotyped with amphotropic and T-tropic envelope glycoprotein, but not with virus lacking envelope glycoprotein (FIG. 2A). Cells transiently transfected with expression vectors for CD4 plus CC-CKR-1, CC-CKR-2B, CC-CKR-3, or CC-CKR-4 are resistant to infection with virus pseudotyped with macrophage-tropic envelopes when compared to vector-transfected control cells (FIG. 2A). However, surprisingly cells co-expressing CD4 and CC-CKR-5 display an increase of three to four orders of magnitude in sensitivity to infection with viruses pseudotyped by ADA, BaL or JRFL envelope glycoproteins (FIG. 2A). Nearly identical findings were observed for CC-CKR-5 cDNAs amplified from three different individuals.

Infection of the 293T cells expressing both CD4 and CC-CKR-5 is completely blocked by the anti-CD4 monoclonal antibody Leu-3a (FIG. 2B). In addition, when pcCD4 is omitted from the transfection, CC-CKR-5 failed to support virus entry (FIG. 2C). Taken together, these findings indicate that CC-CKR-5 and CD4 must function cooperatively to mediate entry of macrophage-tropic virus.

Murine cells transfected with human CD4 are resistant to infection with all tested strains of HIV. To determine whether chemokine receptors could confer susceptibility to infection, the different receptor genes are stably introduced into murine 3T3.CD4 cells. Cells expressing CC-CKR-1 (CCR1), CC-CKR-2B (CCR2B), CC-CKR-3 (CCR3), CC-CKR-4 (CCR4), Duffy, or fusin (CXCR4) are all resistant to infection with HIV-luciferase pseudotyped with macrophage-tropic Envs, but are infected with virus bearing amphotropic Env (FIG. 3a-3c). Expression of CC-CKR-5 permitted infection with the macrophage-tropic pseudotypes, but these cells are resistant to infection mediated by HXB2 Env (FIG. 3a-3c). Only fusin-expressing 3T3.CD4 cells are permissive for infection with this T-tropic virus (FIG. 3a-3c). The chemokine receptors are expressed on the surface of the 3T3.CD4 cells, as assessed by mobilization of intracellular free $Ca^{++}$ in response to the appropriate chemokines (FIG. 3d-3g). Cells expressing CC-CKR-5 (CCR5) responded to RANTES, MIP-1α and MIP-1β, consistent with known β-chemokine reactivities. Infection of the 3T3.CD4 cells expressing CC-CKR-5 with macrophage-tropic virus is blocked by a mixture of the three chemokines that efficiently activate this receptor as well as by anti-CD4 antibody (FIG. 3a-3c). Infection of the fusion-expressing cells with T-tropic virus is also blocked by anti-CD4, but is completely refractory to treatment with chemokines. Thus, these results suggest that only CC-CKR-5 mediates entry of macrophage-tropic Enys, that T-tropic envelope glycoproteins do not use this co-receptor for entry, and that β-chemokines block entry of the macrophage-tropic virus by specifically binding to this receptor.

Stable expression of CC-CKR-5, but not of the other β-chemokine receptors, in human HOS.CD4, HeLa.CD4, and U87MG.CD4 cells also conferred upon these cells susceptibility to infection with macrophage-tropic HIV-1 (FIG. 3h, 3i-3j and data not shown). As observed in the transient transfections, stable co-expression of both CC-CKR-5 and CD4 is required for viral entry into the HeLa cells (FIG. 3i-3j). Infection of these cells with macrophage-tropic virus is reduced by 70–80% upon treatment with a mixture of chemokines (FIG. 3i-3j). High levels of β-chemokines failed to inhibit infection of HOS.CD4 cells. In general, inhibition with β-chemokines is consistently less efficient in the non-lymphoid cells expressing CD4 and CC-CKR-5 than in the PM1 cells.

CC-CKR-5 Promotes Env-Mediated Fusion

Fusion of the HIV-1 envelope with the cellular plasma membrane can be simulated by co-cultivating cells expressing envelope glycoprotein with human cells that express CD4, thus resulting in formation of syncytia. Murine cells expressing human $CD4^+$ fail to support this fusion. Expression of fusin renders murine cells fusogenic for cells expressing T-tropic, but not macrophage-tropic Env. To test whether CC-CKR-5 would support fusion with cells expressing macrophage-tropic Env, 293T cells are transfected with different Env expression vectors and co-cultivated overnight with cell lines stably expressing transfected CD4 and CC-CKR-5 genes. As shown in FIG. 4A-4D, 293T cells expressing JRFL Env formed large syncytia with murine 3T3.CD4 cells expressing CC-CKR-5, but not with cells expressing fusin. Conversely, 293T cells expressing HXB2 Env fused to cells expressing fusin, but not to cells expressing CC-CKR-5. Similar results are obtained with U87MG.CD4 cells transfected with either fusin or CC-CKR-5. Thus, macrophage-tropic Env-mediated fusion occurs in a manner that is highly specific for the entry cofactor.

EXAMPLE 2

Replication of Macrophage-Tropic Virus in Cells Expressing CC-CKR-5

To test whether CC-CKR-5 expression allows for full replication and spread of macrophage-tropic virus, HOS.CD4 cells expressing CC-CKR-5 and control cells (HOS.CD4-BABE, transduced with the puromycin-resistance vector alone) are infected with the replication-competent reporter viruses HIV-HSA and HIV(BaL)-HSA. Both viruses are based on the T-cell line-adapted virus NL4-3, but the latter contains the BaL macrophage-tropic Env. Both viruses replicate in PM1 cells (FIG. 5A) but HIV(BaL)HSA fails to replicate in T-cell lines such as CEMX174 cells and in HOS.CD4. The viruses contain the gene for heat stable antigen (CD24) in place of nef, allowing for quantitation of the infected cells by fluorescence activated cell sorting (FACS) after staining with anti-HSA monoclonal antibody. The HOS.CD4-BABE cells remain uninfected with both viruses six days after infection FIG. 5B, but nearly all of the HOS.CD4-CKR5 cells are infected with HIV(BaL)-HSA (FIG. 5C). Sampling of the HIV(BaL)-HSA infected cultures over a several day period indicate that an increasing percentage of the cells become infected over time, confirming the ability of the virus to spread in the culture (FIG. 5D). HIV-HSA fail to replicate in the HOS.CD4-CKR5 cultures, consistent with the restriction of this T-tropic virus to utilizing fusin, which is likely to be limiting in these cells. Expression of CC-CKR-5 in 3T3.CD4 cells also permits HIV(BaL)HSA virus replication, but this is rather limited, presumably due to inefficient viral gene expression in murine cells.

EXAMPLE 3

CC-CKR-5 is Expressed in Primary T-cells and Macrophages

The initial description of the CC-CKR-5 gene suggested that its expression is limited to granulocyte precursors, and absent in peripheral blood mononuclear cells (PBMC). To be a major co-receptor in vivo, however, this molecule would be expected to be expressed in T-cells and monocytelmacrophages, the predominant cell-types targeted by the virus. Northern blot analysis with CC-CKR-5 cDNA as probe does not readily distinguish between CC-CKR-5 and the closely related CC-CKR-2 transcripts. Reverse-transcriptase PCR is performed on isolated subsets from PBMC. CC-CKR-5 transcripts are detected in both the monocyte/macrophage and macrophage-depleted $CD4^+$ fractions (FIG. 6). In addition, it is found that PM1 and HUT78 cells both express the gene. Significantly more CC-CKR-5 transcript is detected in PM1 cells, consistent with the higher infectivity of these cells by macrophage-tropic and primary HIV-1 isolates.

CC-CKR-5 thus acts as a potent co-receptor, in concert with CD4, to permit entry of macrophage-tropic HIV-1 into cells. Both CD4 and CC-CKR-5 are required for viral entry to proceed, just as CD4 and fusin are required for entry of T cell line-adapted virus. Co-receptor usage appears to be highly sequence specific since the other known members of the β-chemokine receptor family, including CC-CKR-1, 2B, 3, 4, and Duffy antigen show no detectable co-receptor activity for either macrophage- or T-tropic envelope glycoproteins in the viral strains tested. Since a variety of human and murine cells transfected with human CD4 and CC-CKR-5 are efficiently infected with macrophage-tropic virus, this combination of surface molecules is likely to promote infection with primary strains of HIV-1 in vivo. Although the precise expression pattern of CC-CKR-5 is not presently known, it is expressed in T lymphocytes, and the data suggest that it is also present in monocytes and macrophages. However, it remains possible that in these cells a yet unidentified co-receptor is active. Moreover, T-cells could express related proteins other than those tested that could in some cases be used as co-receptors.

The macrophage tropic envelope glycoproteins that are used are derived from virus after limited growth in PBMC and are therefore likely to reflect co-receptor use similar to that of primary virus. This suggests that CC-CKR-5 serves as a major co-receptor for primary macrophage-tropic strains of HIV-1 in vivo. This co-receptor may also be active during HIV-1 transmission, as suggested by the strict predominance of macrophage-tropic virus early in infection. In this regard, a role for chemokine receptors in HIV-1 transmission is suggested by Paxton et al. who showed that the CD4+ cells of individuals to whom HIV-1 cannot be sexually transmitted produce unusually high levels of β-chemokines.

The finding of the role of CC-CKR-5 in macrophage-tropic virus entry, together with the recent identification of fusin as the co-receptor for entry of T-tropic viruses, resolves a long-standing puzzle as to the basis of envelope glycoprotein-related differences in HIV-1 tropism. The adaptation of primary HIV-1 isolates for growth in transformed T cell lines is thus likely to result from a selection for envelope glycoprotein sequences that use fusin rather than CC-CKR-5 as co-receptor. Likewise, the well-documented in vivo phenotypic switch from macrophage-tropic (or NSI) to T-tropic (SI) viruses that occurs in many infected individuals prior to an increase in severity of the disease could be the result of a change in co-receptor usage from CC-CKR-5 to fusin. The appearance of fusin-specific virus could allow for continued virus replication in the presence of high levels of β-chemokine or could result in infection of a wider variety of cell types. With the new tools now available, it will now be possible to carefully evaluate the receptor usage of viruses sampled at different stages of HIV disease progression.

The basis for the change in receptor usage is likely to be determined, at least in part, by changes in specific sequences within the V3 loop of gp120, which has been shown to have a key role in HIV-1 tropism. Furthermore, CD4 binding appears to induce a conformational change in the envelope glycoprotein that increases exposure of the V3 loop. Based on these findings, it is determined that CD4 binding induces a conformational change in Env that exposes a co-receptor binding domain. This domain would then interact with specific amino acid residues on an adjacent co-receptor molecule. A successful interaction could trigger a conformational change in gp41, releasing its amino terminal hydrophobic peptide to initiate membrane fusion. Such a mechanism has precedent in the low pH-mediated activation of influenza hemagglutinin.

A required interaction between CD4 and the chemokine receptor could involve only the first two immunoglobulin-like domains of CD4, since the other domains are dispensable (Bedinger et al). It can also involve the signaling through the chemokine receptor which can be a means of HIV-1 entry and/or a means for a subsequent event in viral replication. The mechanism of chemokine blocking can involve steric hindrance or desensitization of the receptor through down-regulation or conformational changes. The inefficient chemokine blocking that is observed with several cell lines indicates that competition for a binding site on the receptor is not sufficient. Finally, there can be a role for the members of the chemokine receptor family that can interact with HIV envelope glycoprotein in aberrant signal transduction resulting in elimination of T helper cells late in the disease process.

EXAMPLE 4

Use of Chemokine Receptors by Clinical Isolates of HIV-1:

To further study the chemokine receptor specificities of primary viral isolates, the abilities of viruses to infect a panel of U87.CD4 cells that express the various chemokine receptors was determined. Since U87 cells do not express either CCR5 or CXCR4, they are useful for these types of studies. Studies indicate that NSI or slow/low viruses, most of which are derived from individuals with relatively high CD4 cells counts, use exclusively CCR5 for entry. In contrast, SI or rapid/high viruses, isolated from patients with low CD4 cells counts, always use CCR4 but, in addition, often also use CCR5, CCR3, and CCR2B. The broad tropism observed in these isolates is due to mixtures of viruses with different chemokine receptor specificities, but cloned viruses with broad specificities were also identified. In addition, in studies of sequential isolates obtained from infected infants, a clear transition was observed from CCR5-tropic viruses shortly after birth to CXCR4-tropic or polytropic strains after 1–3 years. This provides strong support for the thesis that CCR5-tropic viruses are required for transmission of infection and that they predominate during the early non-symptomatic phase of infection, whereas viruses with broad tropism, but with particular specificity for CXCR4, arise during the onset of immune system disease.

To facilitate analysis of chemokine receptor specificities of primary strains of HIV-1 and of the effectiveness of anti-HIV neutralizing antibodies, a series of cells whose infection can be monitored more easily, and more quantitatively, than that of U87 cells described above, were developed. HOS.CD4 cells, which express only low levels of CXCR4 and no CCR5, were transfected with a construct containing the Green Fluorescent Protein (GFP) under regulation of the HIV-2 LTR. A transfected clone that showed low background fluorescence but had high fluorescence after Tat expression was then transduced with the panel of murine retroviral vectors encoding the various chemokine receptors. Infection of these cells with molecular clones of HIV-1 resulted in high expression of GFP, which can be monitored by FACS analysis (FIG. 3).

LITERATURE CITED

1. Sattentau, Q. J. & Weiss, R. A. Cell 52, 631–633 (1988).
2. Ashorn, P. A., Berger, E. A. & Moss, B. J. Virol. 64, 2149–2156 (1990).
3. Page, K. A., Landau, N. R. & Littman, D. R. J. Virol. 64, 5270–5276 (1990).
4. Maddon, P. J., et al. Cell 47, 333–348 (1986).
5. Cheng-Mayer, C., Weiss, C., Seto, D. & Levy, J. A. Proc. Natl. Acad. Sci. USA 86, 8575–8579 (1989).
6. Koyanagi, Y., et al. Science 236, 819–822 (1987).
7. Liu, Z. Q., Wood, C., Levy, J. A. & Cheng-Mayer, C. J. Virol. 64, 6148–6153 (1990).
8. O'Brien, W. A., et al. Nature 348, 69–73 (1990).
9. Feng, Y., Broder, C. C., Kennedy, P. E. & Berger, E. A. Science 272, 872–877 (1996).
10. Cornelissen. M., et al. J. Virol. 69, 1810–1818 (1995).
11. Veenstra, J., et al. Clin. Infect. Dis. 21, 556–560 (1995).
12. Paxton, W. A., et al. Nat. Med. 2, 412–417 (1996).
13. Cocchi, F., et al. Science 720, 1811–1815 (1996).
14. Ben-Baruch, A., et al. J Biol Chem 1995 Sep 22;270 (38):22123–8 270, 22123–22128 (1995).
15. Neote, K., DiGregorio, D., Mak, J. Y., Horuk, R. & Schall, T. J. Cell 72, 415–25 (1993).
16. Combadiere, C., Ahuja, S. K. & Murphy, P. M. J Biol Chem 270, 16491–4 (1995).
17. Power, C. A., et al. J Biol Chem 270, 19495–500 (1995).
18. Samson, M., Labbe, O., Mollereau, C., Vassart, G. & Parmentier, M. Biochemistry 35, 3362–3367 (1996).
19. Chaudhuri, A., et al. J Biol Chem 269, 7835–8 (1994).
20. Jazin, E. E., et al. Regul. Pept. 47, 247–258 (1993).
21. Lusso, P., et al. J. Virol. 69, 3712–3720 (1995).
22. Connor, R. I., Chen, B. K., Choe, S. & Landau, N. R. Virology 206, 936–944 (1995).
23. Westervelt, P., Gendelman, H. E. & Ratner, L. Proc. Natl. Acad. Sci. USA 88, 3097–101 (1991).

24. Hwang, S. S. Boyle, T. J. Lyerly, H. K. & Cullen, B. R. Science 253, 71–74 (1991).
25. Landau, N. R., Page, K. A. & Littman, D. R. J. Virol. 65, 162–169 (1991).
26. He, J., et al. J. Virol. 69, 6705–6711 (1995).
27. Zhu, T., et al. Science 261, 1179–1181 (1993).
28. Schuitemaker, H., et al. J. Virol. 66, 1354–60 (1992).
29. Connor, R. I. & Ho, D. D. J. Virol. 68, 4400–4408 (1994).
30. De Jong, J. J., De Ronde, A., Keulen, W., Tersmette, M. & Goudsmit, J. J. Virol. 66, 6777–6780 (1992).
31. Fouchier, R. A., et al. J. Virol. 66, 3183–3187 (1992).
32. Sattentau, Q. J., Moore, J. P., Vignaux, F., Traincard, F. & Poignard, P. J. Virol. 67, 7383–7393 (1993).
33. Bullough, P. A., Hughson, F. M., Skehel, J. J. & Wiley, D.C. Nature 371, 37–43 (1994).
34. Bedinger, P., et al. nature 334, 162–165 (1988).
35. Morgenstern. J. P. & Land, H. Nucl. Acids Res. 18, 3587–3596 (1990).
36. Landau, N. R., Warton, M. & Littman, D. R. Nature 334, 159–162 (1988).
37. Landau, N. R. & Littman, D. R. J. Virol. 66, 5110–5113 (1992).
38. Pear, W. S., Nolan, G. P., Scott, M. L. & Baltimore, D. Proc. Natl. Acad. Sci. USA 90, 8392–8396 (1994).
39. Killeen, N., Sawada, S. and Littman, D. R. EMBO 12 1547–1553 (1993).
40. Hogan, B. L. M., Costantini, F. and Lacy, E. *Manipulating the Mouse Embryo*. Cold Spring Harbor Laboratory Press, Cold Spring Harbor, N.Y. (1986)
41. Hanks, M., Wurst, W., Anson-Cartwright, L. Auerbach, A. B., and Joiner, A. L. Science 269, 679–682 (1995).
42. Dimitrov, D. S. Nature Medicine 2 640–641 (1996).

While the invention has been described and illustrated herein by references to various specific material, procedures and examples, it is understood that the invention is not restricted to the particular material combinations of material, and procedures selected for that purpose. Numerous variations of such details can be implied as will be appreciated by those skilled in the art.

Various publications are cited herein, the disclosures of which are incorporated by reference in their entireties.

What is claimed is:

1. A method of identifying an agent that inhibits entry of a macrophage-tropic HIV virus into a target cell, wherein said entry of the macrophage-tropic HIV into said target cell is a fusion process mediated by CC-CKR5 and CD4 expressed on the surface of said target cell, the method comprising the steps of:

(a) contacting said target cell with a virus pseudotyped with a macrophage-tropic HIV envelope in the presence or absence of said agent;

(b) measuring the fusion between the virus pseudotyped with a macrophage-tropic HIV envelope and said target cell, wherein the measurement of said fusion is performed by a fluorescence intensity detection or by a fluorescence activated cell sorting (FACS) analysis, and (c) determining whether said fusion of the virus pseudotyped with a macrophage-tropic HIV envelope is inhibited in the presence of the agent but not in the absence of the agent.

* * * * *

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Homo sapiens (xi) SEQUENCE DESCRIPTION: SEQ ID NO: 1:

CTCGGATCCG GTGGAACAAG ATGGATTAT                                29

(2) INFORMATION FOR SEQ ID NO: 2:

(i) SEQUENCE CHARACTERISTICS:
      (A) LENGTH: 28 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (vi) ORIGINAL SOURCE:
      (A) ORGANISM: Homo sapiens (xi) SEQUENCE DESCRIPTION: SEQ ID NO: 2:

CTCGTCGACA TGTGCACAAC TCTGACTG                                 28

(2) INFORMATION FOR SEQ ID NO: 3:

(i) SEQUENCE CHARACTERISTICS:
      (A) LENGTH: 66 base pairs (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO: 3:

ATGGATTATC AAGTGTCAAG TCCAATCTAT GACATCAATT ATTATACATC GGAGCCCTGC      60

CAAAAA                                                                66

(2) INFORMATION FOR SEQ ID NO: 4:

(i) SEQUENCE CHARACTERISTICS:
        (A) LENGTH: 22 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Homo sapiens (xi) SEQUENCE DESCRIPTION: SEQ ID NO: 4:

Met Asp Tyr Gln Val Ser Ser Pro Ile Tyr Asp Ile Asn Tyr Tyr Thr
1               5                   10                  15

Ser Glu Pro Cys Gln Lys
            20

(2) INFORMATION FOR SEQ ID NO: 5:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO: 5:

ATGGATTATC AAGTGTCAAG TCCAATCTAT GACATCAATT ATCCATACGA TGTTCCAGAT      60

TATGCTTCGG AGCCCTGCCA AAAA                                            84

(2) INFORMATION FOR SEQ ID NO: 6:

(i) SEQUENCE CHARACTERISTICS:
        (A) LENGTH: 28 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 6:

```
Met Asp Tyr Gln Val Ser Ser Pro Ile Tyr Asp Ile Asn Tyr Pro Tyr
1               5                   10                  15

Asp Val Pro Asp Tyr Ala Ser Glu Pro Cys Gln Lys
            20                  25
```

(2) INFORMATION FOR SEQ ID NO: 7:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (vi) ORIGINAL SOURCE:
        (A) ORGANISM: Homo sapiens (xi) SEQUENCE DESCRIPTION: SEQ ID NO: 7:

```
ATCAATTATC CATACGATGT TCCAGATTAT GCTTCGGAGC CCTGCCAAAA A        51
```

(2) INFORMATION FOR SEQ ID NO: 8:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Oligonucleotides"

(iii) HYPOTHETICAL: NO (vi) ORIGINAL SOURCE:
        (A) ORGANISM: Homo sapiens (xi) SEQUENCE DESCRIPTION: SEQ ID NO: 8:

```
GCAGGATCCA CCATGGATTA TCAAGTGTCA AGTCCAATCT ATGACATCAA TTATCCATAC        60

GAT                                                                     63
```

(2) INFORMATION FOR SEQ ID NO: 9:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (xi) SEQUENCE DESCRIPTION: SEQ ID NO: 9:

```
CCATACGATG TTCCAGATTA TGCT                                              24
```

(2) INFORMATION FOR SEQ ID NO: 10:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 10:

Pro Tyr Asp Val Pro Asp Tyr Ala
1               5

(2) INFORMATION FOR SEQ ID NO: 11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO: 11:

TATCCATACG ATGTTCCAGA TTATGCTTCG                                    30

(2) INFORMATION FOR SEQ ID NO: 12:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO: 12:

Tyr Pro Tyr Asp Val Pro Asp Tyr Ala Ser
1               5                   10

(2) INFORMATION FOR SEQ ID NO: 13:

(i) SEQUENCE CHARACTERISTICS:
        (A) LENGTH: 3383 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO: 13:

AGAAGAGCTG AGACATCCGT TCCCCTACAA GAAACTCTCC CCGGGTGGAA CAAGATGGAT     60

TATCAAGTGT CAAGTCCAAT CTATGACATC AATTATTATA CATCGGAGCC CTGCCAAAAA    120

ATCAATGTGA AGCAAATCGC AGCCCGCCTC CTGCCTCCGC TCTACTCACT GGTGTTCATC    180

TTTGGTTTTG TGGGCAACAT GCTGGTCATC CTCATCCTGA TAAACTGCAA AAGGCTGAAG    240

AGCATGACTG ACATCTACCT GCTCAACCTG GCCATCTCTG ACCTGTTTTT CCTTCTTACT    300

GTCCCCTTCT GGGCTCACTA TGCTGCCGCC CAGTGGGACT TTGGAAATAC AATGTGTCAA    360

CTCTTGACAG GGCTCTATTT TATAGGCTTC TTCTCTGGAA TCTTCTTCAT CATCCTCCTG    420

ACAATCGATA GGTACCTGGC TGTCGTCCAT GCTGTGTTTG CTTTAAAAGC CAGGACGGTC    480

| | |
|---|---|
| ACCTTTGGGG TGGTGACAAG TGTGATCACT TGGGTGGTGG CTGTGTTTGC GTCTCTCCCA | 540 |
| GGAATCATCT TTACCAGATC TCAAAAAGAA GGTCTTCATT ACACCTGCAG CTCTCATTTT | 600 |
| CCATACAGTC AGTATCAATT CTGGAAGAAT TTCCAGACAT TAAAGATAGT CATCTTGGGG | 660 |
| CTGGTCCTGC CGCTGCTTGT CATGGTCATC TGCTACTCGG GAATCCTAAA AACTCTGCTT | 720 |
| CGGTGTCGAA ATGAGAAGAA GAGGCACAGG GCTGTGAGGC TTATCTTCAC CATCATGATT | 780 |
| GTTTATTTTC TCTTCTGGGC TCCCTACAAC ATTGTCCTTC TCCTGAACAC CTTCCAGGAA | 840 |
| TTCTTTGGCC TGAATAATTG CAGTAGCTCT AACAGGTTGG ACCAAGCTAT GCAGGTGACA | 900 |
| GAGACTCTTG GGATGACGCA CTGCTGCATC AACCCCATCA TCTATGCCTT TGTCGGGGAG | 960 |
| AAGTTCAGAA ACTACCTCTT AGTCTTCTTC CAAAAGCACA TTGCCAAACG CTTCTGCAAA | 1020 |
| TGCTGTTCTA TTTTCCAGCA AGAGGCTCCC GAGCGAGCAA GCTCAGTTTA CACCCGATCC | 1080 |
| ACTGGGGAGC AGGAAATATC TGTGGGCTTG TGACACGGAC TCAAGTGGGC TGGTGACCCA | 1140 |
| GTCAGAGTTG TGCACATGGC TTAGTTTTCA TACACAGCCT GGGCTGGGGG TGGGGTGGGA | 1200 |
| GAGGTCTTTT TTAAAAGGAA GTTACTGTTA TAGAGGGTCT AAGATTCATC CATTTATTTG | 1260 |
| GCATCTGTTT AAAGTAGATT AGATCTTTTA AGCCCATCAA TTATAGAAAG CCAAATCAAA | 1320 |
| ATATGTTGAT GAAAAATAGC AACCTTTTTA TCTCCCCTTC ACATGCATCA AGTTATTGAC | 1380 |
| AAACTCTCCC TTCACTCCGA AAGTTCCTTA TGTATATTTA AAAGAAAGCC TCAGAGAATT | 1440 |
| GCTGATTCTT GAGTTTAGTG ATCTGAACAG AAATACCAAA ATTATTTCAG AAATGTACAA | 1500 |
| CTTTTTACCT AGTACAAGGC AACATATAGG TTGTAAATGT GTTTAAAACA GGTCTTTGTC | 1560 |
| TTGCTATGGG GAGAAAAGAC ATGAATATGA TTAGTAAAGA AATGACACTT TCATGTGTG | 1620 |
| ATTTCCCCTC CAAGGTATGG TTAATAAGTT TCACTGACTT AGAACCAGGC GAGAGACTTG | 1680 |
| TGGCCTGGGA GAGCTGGGGA AGCTTCTTAA ATGAGAAGGA ATTTGAGTTG GATCATCTAT | 1740 |
| TGCTGGCAAA GACAGAAGCC TCACTGCAAG CACTGCATGG GCAAGCTTGG CTGTAGAAGG | 1800 |
| AGACAGAGCT GGTTGGGAAG ACATGGGGAG GAAGGACAAG GCTAGATCAT GAAGAACCTT | 1860 |
| GACGGCATTG CTCCGTCTAA GTCATGAGCT GAGCAGGGAG ATCCTGGTTG GTGTTGCAGA | 1920 |
| AGGTTTACTC TGTGGCCAAA GGAGGGTCAG GAAGGATGAG CATTTAGGGC AAGGAGACCA | 1980 |
| CCAACAGCCC TCAGGTCAGG GTGAGGATGG CCTCTGCTAA GCTCAAGGCG TGAGGATGGG | 2040 |
| AAGGAGGGAG GTATTCGTAA GGATGGGAAG GAGGGAGGTA TTCGTGCAGC ATATGAGGAT | 2100 |
| GCAGAGTCAG CAGAACTGGG GTGGATTTGG TTTGGAAGTG AGGGTCAGAG AGGAGTCAGA | 2160 |
| GAGAATCCCT AGTCTTCAAG CAGATTGGAG AAACCCTTGA AAAGACATCA AGCACAGAAG | 2220 |
| GAGGAGGAGG AGGTTTAGGT CAAGAAGAAG ATGGATTGGT GTAAAAGGAT GGGTCTGGTT | 2280 |
| TGCAGAGCTT GAACACAGTC TCACCCAGAC TCCAGGCTGT CTTTCACTGA ATGCTTCTGA | 2340 |
| CTTCATAGAT TTCCTTCCCA TCCCAGCTGA AATACTGAGG GGTCTCCAGG AGGAGACTAG | 2400 |
| ATTTATGAAT ACACGAGGTA TGAGGTCTAG GAACATACTT CAGCTCACAC ATGAGATCTA | 2460 |
| GGTGAGGATT GATTACCTAG TAGTCATTTC ATGGGTTGTT GGGAGGATTC TATGAGGCAA | 2520 |
| CCACAGGCAG CATTTAGCAC ATACTACACA TTCAATAAGC ATCAAACTCT TAGTTACTCA | 2580 |
| TTCAGGGATA GCACTGAGCA AAGCATTGAG CAAAGGGGTC CCATATAGGT GAGGGAAGCC | 2640 |
| TGAAAAACTA AGATGCTGCC TGCCCAGTGC ACACAAGTGT AGGTATCATT TTCTGCATTT | 2700 |
| AACCGTCAAT AGGCAAAGGG GGGAAGGGAC ATATTCATTT GGAAATAAGC TGCCTTGAGC | 2760 |
| CTTAAAACCC ACAAAAGTAC AATTTACCAG CCTCCGTATT TCAGACTGAA TGGGGGTGGG | 2820 |
| GGGGGCGCCT TAGGTACTTA TTCCAGATGC CTTCTCCAGA CAAACCAGAA GCAACAGAAA | 2880 |

-continued

```
AAATCGTCTC TCCCTCCCTT TGAAATGAAT ATACCCCTTA GTGTTTGGGT ATATTCATTT    2940

CAAAGGGAGA GAGAGAGGTT TTTTTCTGTT CTTTCTCATA TGATTGTGCA CATACTTGAG    3000

ACTGTTTTGA ATTTGGGGGA TGGCTAAAAC CATCATAGTA CAGGTAAGGT GAGGGAATAG    3060

TAAGTGGTGA GAACTACTCA GGGAATGAAG GTGTCAGAAT AATAAGAGGT GCTACTGACT    3120

TTCTCAGCCT CTGAATATGA ACGGTGAGCA TTGTGGCTGT CAGCAGGAAG CAACGAAGGG    3180

AAATGTCTTT CCTTTTGCTC TTAAGTTGTG GAGAGTGCAA CAGTAGCATA GGACCCTACC    3240

CTCTGGGCCA AGTCAAAGAC ATTCTGACAT CTTAGTATTT GCATATTCTT ATGTATGTGA    3300

AAGTTACAAA TTGCTTGAAA GAAAATATGC ATCTAATAAA AACACCTTC TAAAATAAAA     3360

AAAAAAAAAA AAAAAAAAA AAA                                             3383
```

(2) INFORMATION FOR SEQ ID NO: 14:

(i) SEQUENCE CHARACTERISTICS:
        (A) LENGTH: 352 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: Homo sapiens (xi) SEQUENCE DESCRIPTION: SEQ ID NO: 14:

```
Met Asp Tyr Gln Val Ser Ser Pro Ile Tyr Asp Ile Asn Tyr Tyr Thr
 1               5                  10                  15

Ser Glu Pro Cys Gln Lys Ile Asn Val Lys Gln Ile Ala Ala Arg Leu
                20                  25                  30

Leu Pro Pro Leu Tyr Ser Leu Val Phe Ile Phe Gly Phe Val Gly Asn
            35                  40                  45

Met Leu Val Ile Leu Ile Leu Ile Asn Cys Lys Arg Leu Lys Ser Met
        50                  55                  60

Thr Asp Ile Tyr Leu Leu Asn Leu Ala Ile Ser Asp Leu Phe Phe Leu
65                  70                  75                  80

Leu Thr Val Pro Phe Trp Ala His Tyr Ala Ala Ala Gln Trp Asp Phe
                85                  90                  95

Gly Asn Thr Met Cys Gln Leu Leu Thr Gly Leu Tyr Phe Ile Gly Phe
                100                 105                 110

Phe Ser Gly Ile Phe Phe Ile Ile Leu Leu Thr Ile Asp Arg Tyr Leu
            115                 120                 125

Ala Val Val His Ala Val Phe Ala Leu Lys Ala Arg Thr Val Thr Phe
        130                 135                 140

Gly Val Val Thr Ser Val Ile Thr Trp Val Val Ala Val Phe Ala Ser
145                 150                 155                 160

Leu Pro Gly Ile Ile Phe Thr Arg Ser Gln Lys Glu Gly Leu His Tyr
                165                 170                 175

Thr Cys Ser Ser His Phe Pro Tyr Ser Gln Tyr Gln Phe Trp Lys Asn
                180                 185                 190

Phe Gln Thr Leu Lys Ile Val Ile Leu Gly Leu Val Leu Pro Leu Leu
            195                 200                 205

Val Met Val Ile Cys Tyr Ser Gly Ile Leu Lys Thr Leu Leu Arg Cys
        210                 215                 220
```

-continued

```
Arg Asn Glu Lys Lys Arg His Arg Ala Val Arg Leu Ile Phe Thr Ile
225             230             235             240

Met Ile Val Tyr Phe Leu Phe Trp Ala Pro Tyr Asn Ile Val Leu Leu
            245             250             255

Leu Asn Thr Phe Gln Glu Phe Phe Gly Leu Asn Asn Cys Ser Ser Ser
            260             265             270

Asn Arg Leu Asp Gln Ala Met Gln Val Thr Glu Thr Leu Gly Met Thr
        275             280             285

His Cys Cys Ile Asn Pro Ile Ile Tyr Ala Phe Val Gly Glu Lys Phe
    290             295             300

Arg Asn Tyr Leu Leu Val Phe Phe Gln Lys His Ile Ala Lys Arg Phe
305             310             315             320

Cys Lys Cys Cys Ser Ile Phe Gln Gln Glu Ala Pro Glu Arg Ala Ser
            325             330             335

Ser Val Tyr Thr Arg Ser Thr Gly Glu Gln Glu Ile Ser Val Gly Leu
            340             345             350
```